United States Patent
Gazit et al.

(10) Patent No.: US 12,232,949 B2
(45) Date of Patent: Feb. 25, 2025

(54) METHOD OF ENDOGENOUS STEM CELL ACTIVATION FOR TENDON/LIGAMENT OSSEOINTEGRATION

(71) Applicant: Cedars-Sinai Medical Center, Los Angeles, CA (US)

(72) Inventors: Dan Gazit, Los Angeles, CA (US); Gadi Pelled, Los Angeles, CA (US); Thomas Kremen, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 374 days.

(21) Appl. No.: 16/080,852

(22) PCT Filed: Feb. 28, 2017

(86) PCT No.: PCT/US2017/020033
§ 371 (c)(1),
(2) Date: Aug. 29, 2018

(87) PCT Pub. No.: WO2017/151674
PCT Pub. Date: Sep. 8, 2017

(65) Prior Publication Data
US 2019/0083231 A1 Mar. 21, 2019

Related U.S. Application Data

(60) Provisional application No. 62/301,176, filed on Feb. 29, 2016.

(51) Int. Cl.
*A61F 2/08* (2006.01)
*A61K 38/18* (2006.01)
(Continued)

(52) U.S. Cl.
CPC ............. *A61F 2/08* (2013.01); *A61K 38/1875* (2013.01); *A61L 27/24* (2013.01); *A61L 27/54* (2013.01);
(Continued)

(58) Field of Classification Search
CPC ....... A61F 2/08; A61K 38/1875; A61L 27/24; A61L 27/54; A61L 2300/258; A61L 2300/414; A61L 2430/10
See application file for complete search history.

(56) References Cited

U.S. PATENT DOCUMENTS 5,763,416 A * 6/1998 Bonadio et al. ....... C12N 15/00
514/44
8,870,954 B2 10/2014 Lynch et al.
(Continued)

FOREIGN PATENT DOCUMENTS

| CN | 101385851 A | 3/2009 |
| CN | 102231992 A | 11/2011 |

(Continued)

OTHER PUBLICATIONS

Park et al., Biomaterials 28 (2007) 2772-2782.*
(Continued)

*Primary Examiner* — Arthur S Leonard
*Assistant Examiner* — Joseph Paul Miano
(74) *Attorney, Agent, or Firm* — NIXON PEABODY LLP

(57) ABSTRACT

Tendon and ligament injuries are common in orthopaedic clinical practice and cause substantial morbidity in sports and in routine daily activities. While surgical reconstruction is effective, the majority of patients suffer from a prolonged period of recovery because of limited regeneration capacity of the tendon-bone interface. Here, the Inventors have established an approach for promoting tendon/ligament integration. By first recruiting endogenous stem cells to the site
(Continued)

of injury, bone morphogenic proteins (BMPs), are then delivered in vivo to promote repair. Significant acceleration of healing via the above methods and compositions leads to fast recovery and return to normal activities, thereby providing new therapeutic avenues for treatment of injuries involving the tendon-bone interface.

14 Claims, 25 Drawing Sheets

(51) Int. Cl.
  *A61L 27/24*   (2006.01)
  *A61L 27/54*   (2006.01)
(52) U.S. Cl.
  CPC ... *A61L 2300/258* (2013.01); *A61L 2300/414* (2013.01); *A61L 2430/10* (2013.01)

(56) References Cited

U.S. PATENT DOCUMENTS

| | | | |
|---|---|---|---|
| 2011/0124716 A1 | 5/2011 | Passineau | |
| 2014/0178346 A1 | 6/2014 | James et al. | |
| 2014/0277569 A1* | 9/2014 | Lange | A61F 2/28 623/23.51 |
| 2015/0320519 A1 | 11/2015 | Suttin et al. | |

FOREIGN PATENT DOCUMENTS

| | | |
|---|---|---|
| CN | 201780013826.3 | 10/2018 |
| EP | 2674172 A1 | 12/2013 |
| JP | 2019-510750 | 4/2019 |
| WO | 2003029429 A2 | 4/2003 |
| WO | 2017151674 A | 9/2017 |

OTHER PUBLICATIONS

Betz et al., Gene Therapy, 14: 1039-1044, 2007.*
Ratcliffe et al., Annals of Biomedical Engineering, vol. 43, No. 3, Mar. 2015 ( 2015) pp. 819-831.*
Kang et al. Characterization of the distinct orthotopic bone-forming activity of 15 BMPs using recombinant adenovirus-mediated gene delivery, Gene Therapy, 11: 1312-1320. (Year: 2004).*
Watrin-Pinzano, et al., Evaluation of cartilage repair tissue after biomaterial implantation in rat patella by using T2 mapping, Magnetic Resonance Materials in Physics, Biology and Medicine, 17: 219-228 (Year: 2004).*
Delalande et al., Sonoporation: mechanism insights and ongoing challenges for gene transfer, Gene, 525: 191-199. (Year: 2013).*
Umebayasi et al., Gene-activated matrix comprised of atelocollagen and plasmid DBA encoding BMP4 or Runx2 promotes rat cranial bone augmentation, BioResearch Open Access, 4.1:164-174. (Year: 2015).*
Shoaib et al., A comparison of radiation exposure with the conventional versus mini C arm in orthopedic extremity surgery, Foot and Ankle international, p. 58-61. (Year: 2008).*
Hoher et al., Bone tunnel enlargement after anterior cruciate ligament reconstruction: fact or fiction?, Knee Surg, Sports Traumatol, Arthrosc, 6: 231-240. (Year: 1998).*
Shapiro et al., Ultrasound-mediated transgene expression in endogenous stem cells recruited to bone injury sites, Polymers Advanced Technologies, p. 1-7. (Year: 2014).*
Sheyn et al., Ultrasound-based nonviral gene delivery induces bone formation in vivo, Gene Ther., 2008, vol. 15, pp. 257-266.
Feichtinger et al., Sonoporation increases therapeutic efficacy of inducible and constitutive BMP2/7 in vivo gene delivery, Hum Gene Ther Methods, 2014, vol. 25, 57-71.
Ko et al., In situ tissue regeneration through host stem cell recruitment, Exp Mol Med, 2013, pp. 45-57.
Chaudhury, Mesenchymal stem cell applications to tendon healing, Muscles Ligaments Tendons J., 2012, vol. 2, pp. 222-229.
Rothrauff et al., Cellular therapy in bone-tendon interface regeneration, Organogenesis, 2014, vol. 10, pp. 13-28.
Extended Europen Search Report for EP 17760656 dated Oct. 15, 2019, 10 pages.
Hernot et al., Microbubbles in the ultrasound-triggered drug and gene delivery, Advanced Drug Delivery Reviews, 2008, vol. 60(10), pp. 1153-1166.
Ruschke et al., BMPs are mediators in tissue crosstalk of the regenerating musculoskeletal system, Cell and Tissue Research, 2012, vol. 347(3), pp. 521-544.
Marmotti et al., Bone marrow derived stem cellsw in joint and bone diseases: a concise review, International Orthopeadics, 2014, vol. 38(9), pp. 1787-1801.
Sonia et al., Strategies to engineer tendon/ligament-to-bone interface: Biomaterials, cells and growth factors, Advanced Drug Delivery Reviews, 2015, vol. 94, pp. 126-140.
CN OA for 201780013826.3 dated Sep. 21, 2020.
EPO Exam Report for Application No. 17760656.3 dated Aug. 4, 2020.
Tellado et al., Strategies to engineer tendon/ligament-to-bone interface: Biomaterials, cells and growth factors, Advanced Drug Delivery Reviews, 2015, vol. 94, pp. 126-140.
Shapiro et al., Therapeutic Gene Targeting To Endogenous Stem Cells For Bone Regeneration, 2014 Poster abstract, Orthopaedic Research Society (ORS) 60th Annual Meeting, New Orleans, LA, 2014.
International Search Report and Written Opinion of PCT/US2017/020033, Dated Jul. 27, 2017, 11 Pages.
Chen, G et al., Cell-free scaffolds with different stiffness but same microstructure promote bone regeneration in rabbit large bone defect model, Journal of Biomedical Materials Research. Part A, 2015, vol. 104(4), p. 833-884.
Kovacevic et al., Biological augmentation of rotator cuff tendon repair, Clin Orthop Relat Res., 2008, vol. 466, pp. 622-633.

* cited by examiner

Figure 4
Fig. 4A
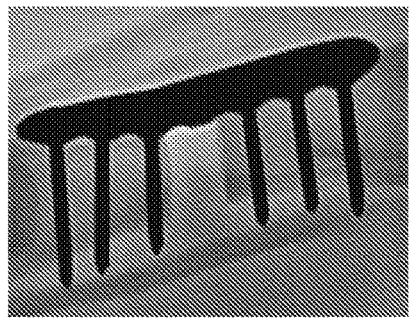
Fig. 4B
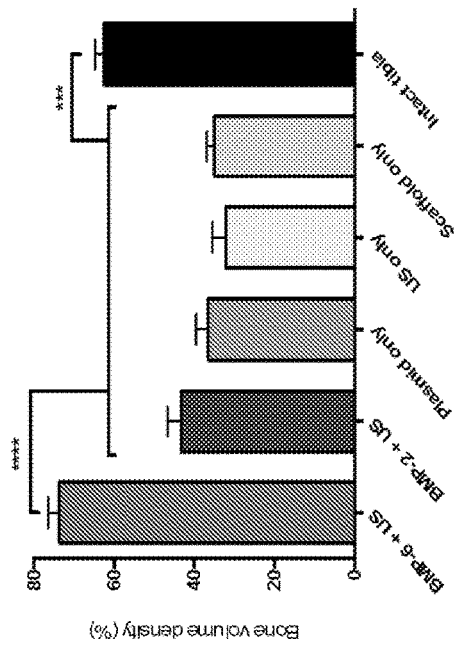
Fig. 4C
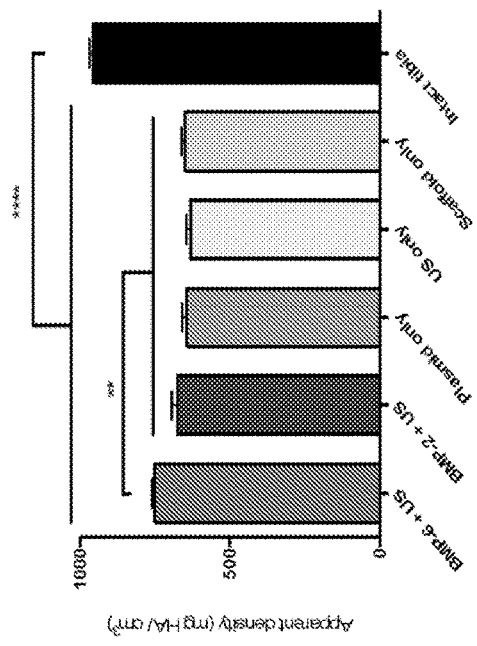

Figure 7
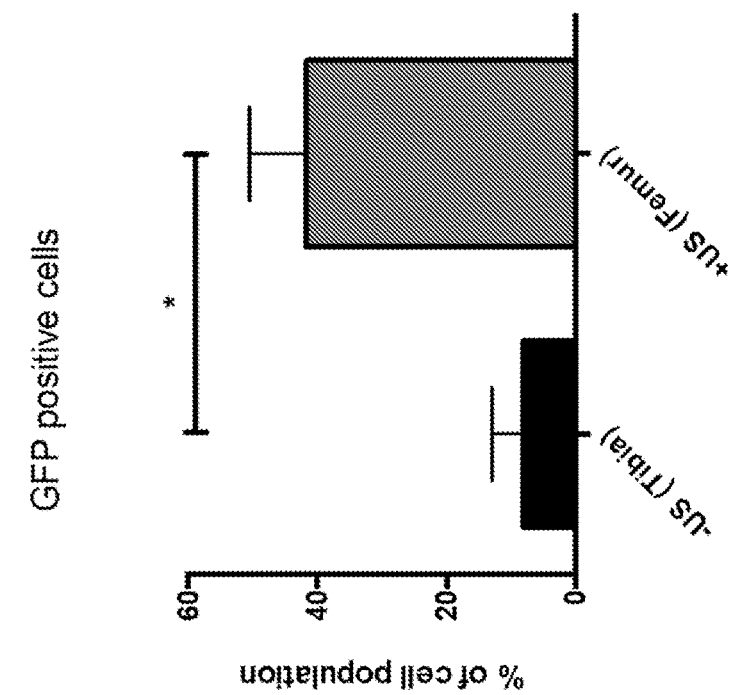
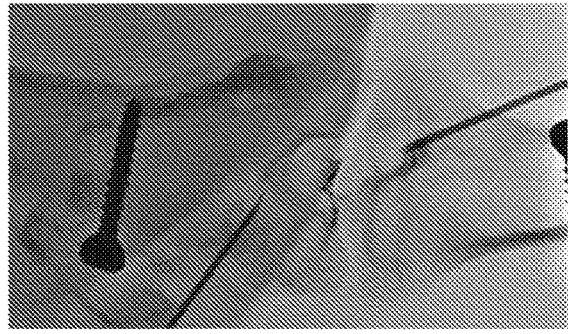
Fig. 7A
Fig. 7B
Fig. 7C

Figure 8
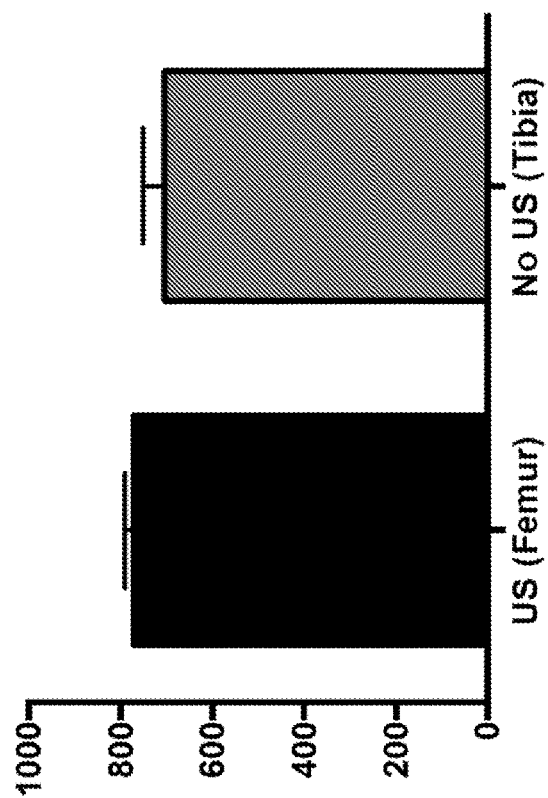
Fig. 8B
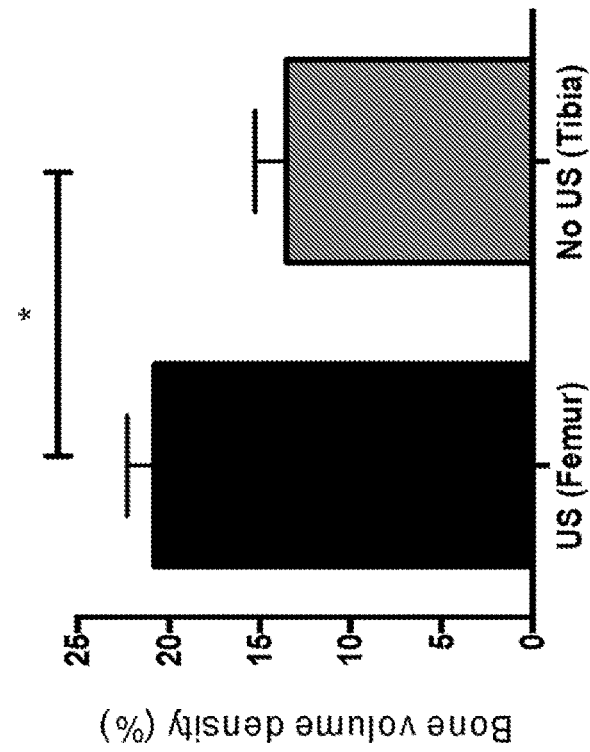
Fig. 8A

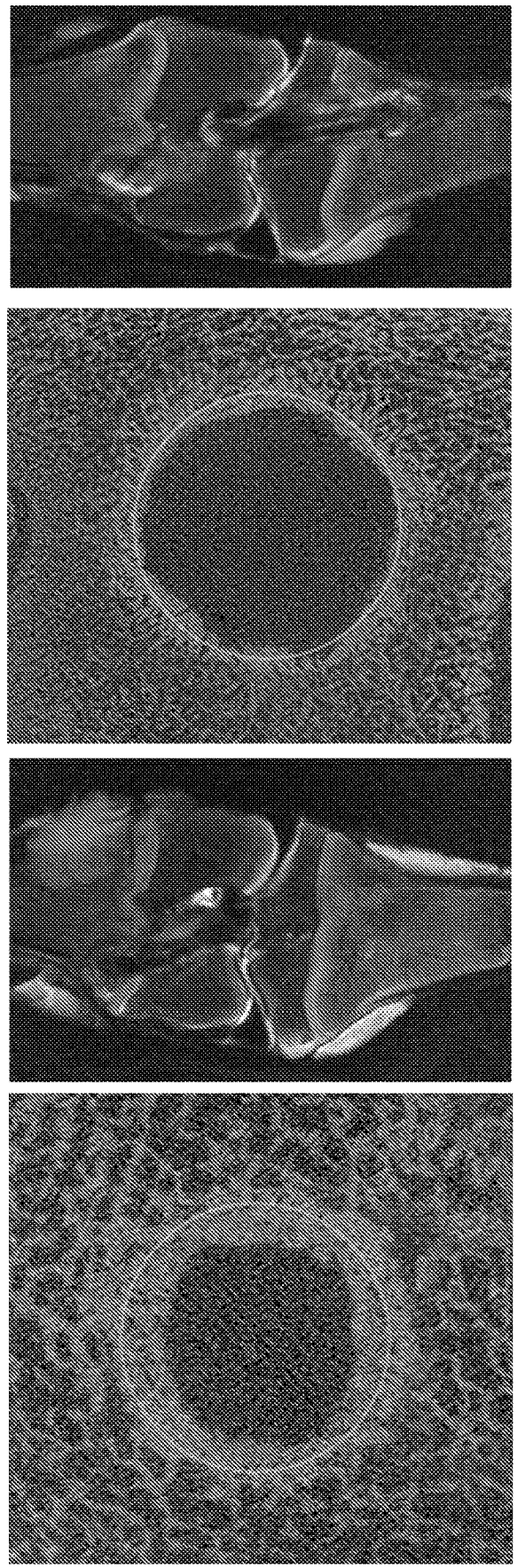

Figure 10
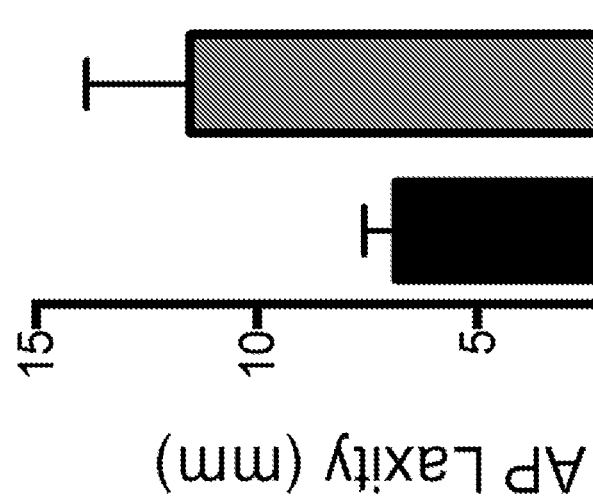
Fig. 10A
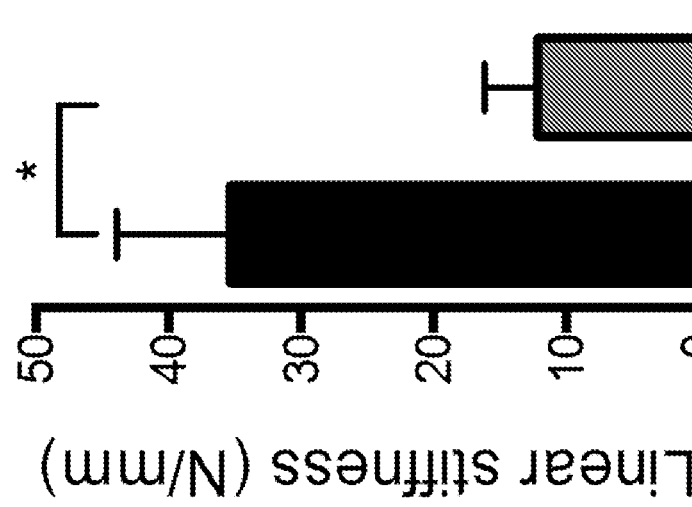
Fig. 10B
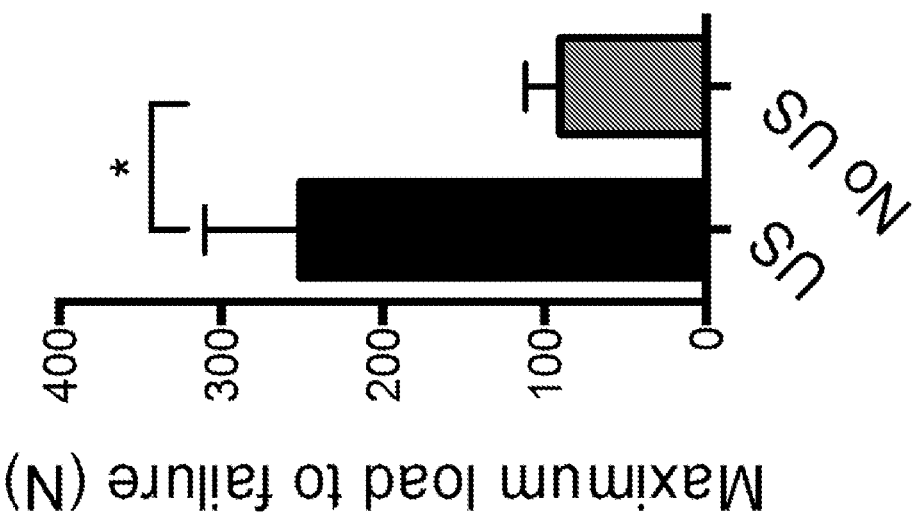
Fig. 10C

Figure 12
Fig. 12A
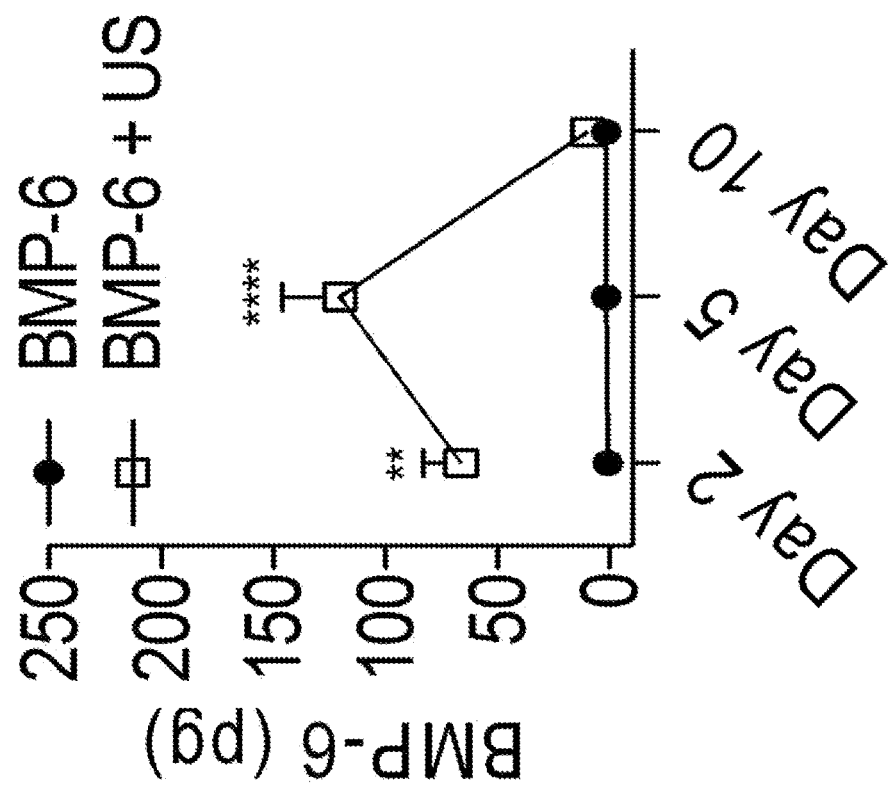
Fig. 12B
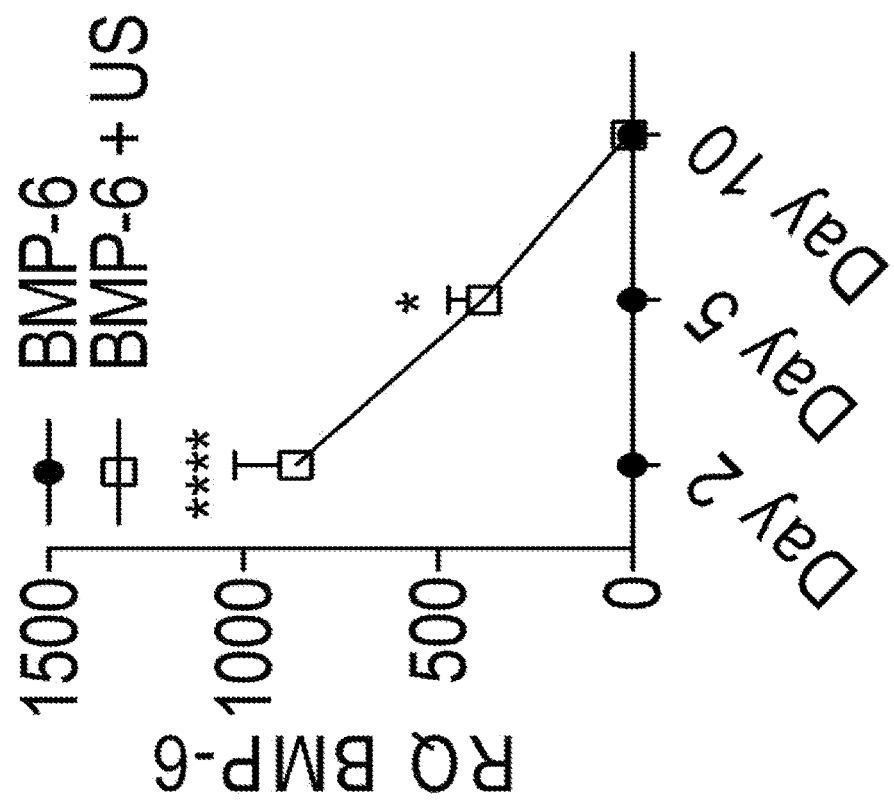

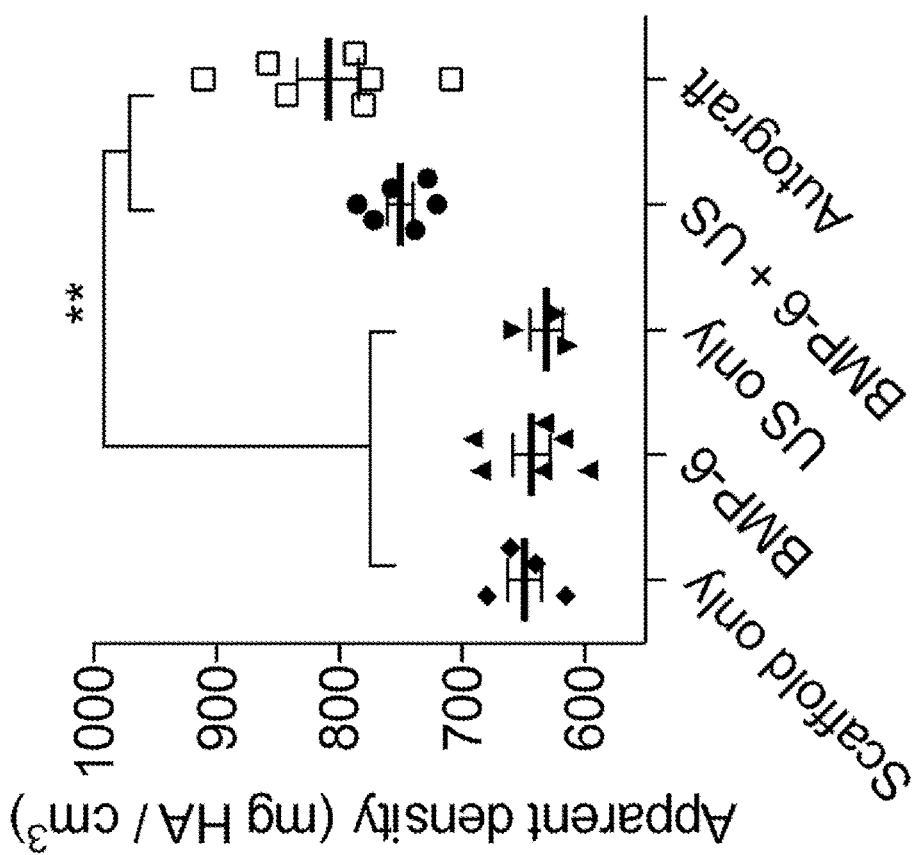
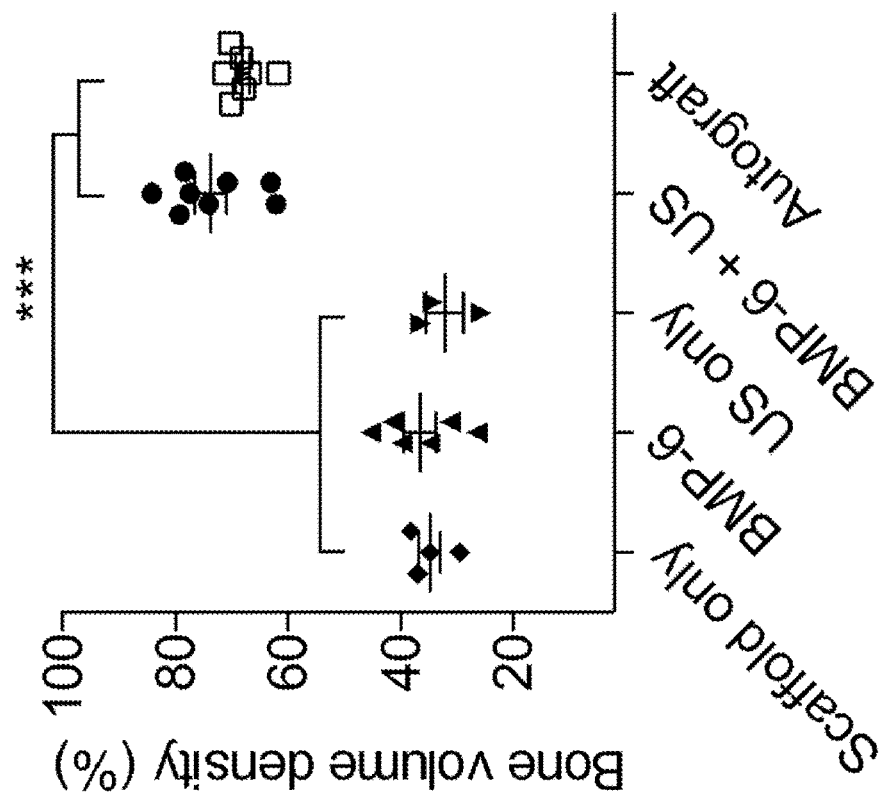
Figure 13
Fig. 13A
Fig. 13B

Figure 14
Fig. 14A
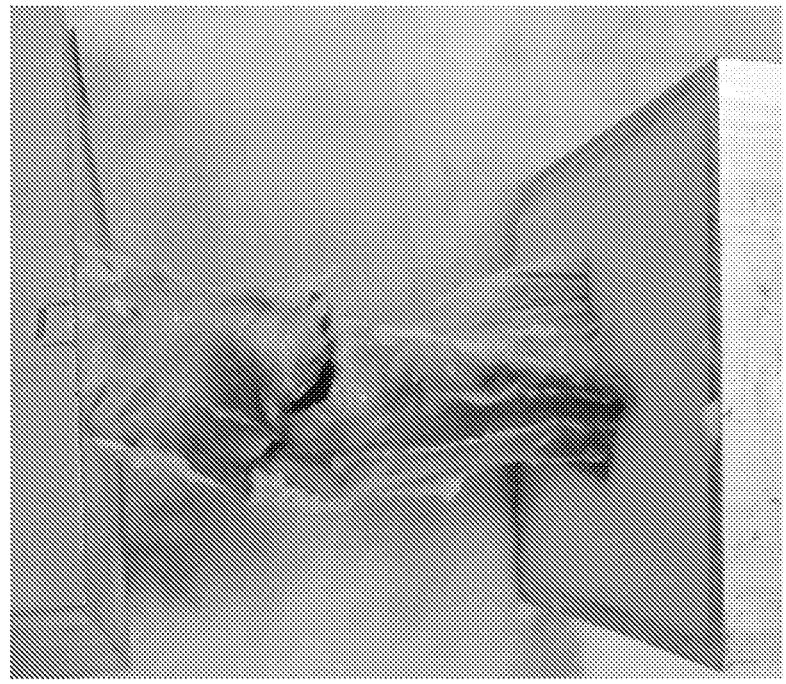
Fig. 14B
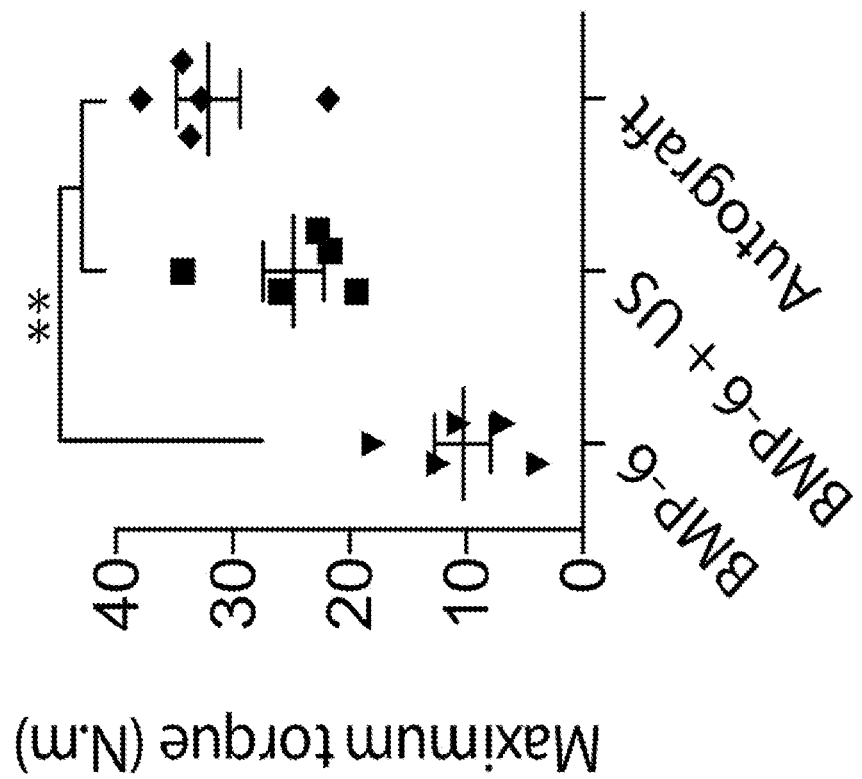

Figure 14
Fig. 14C
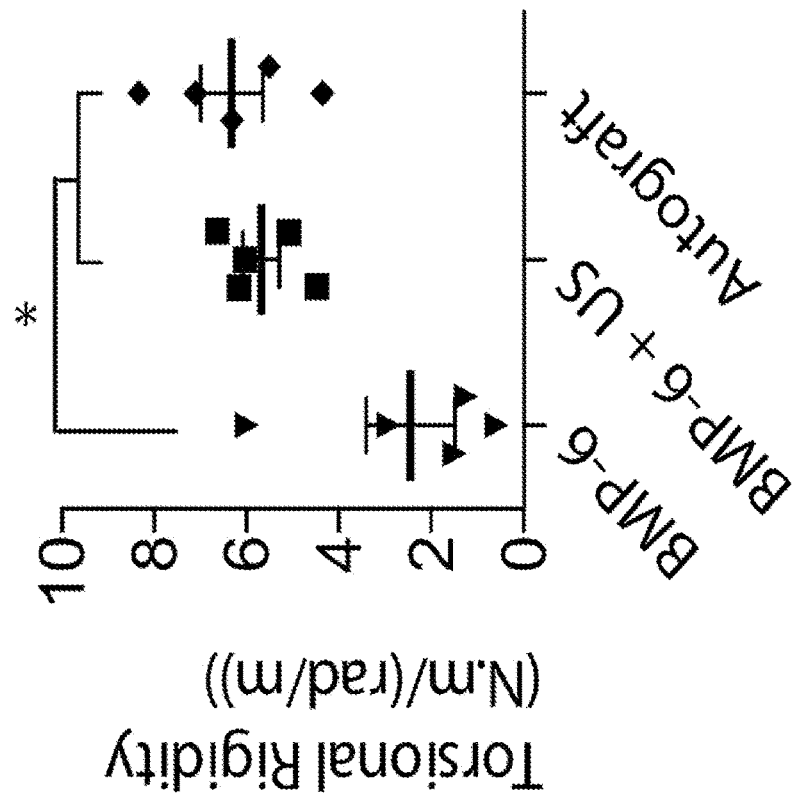
Fig. 14D
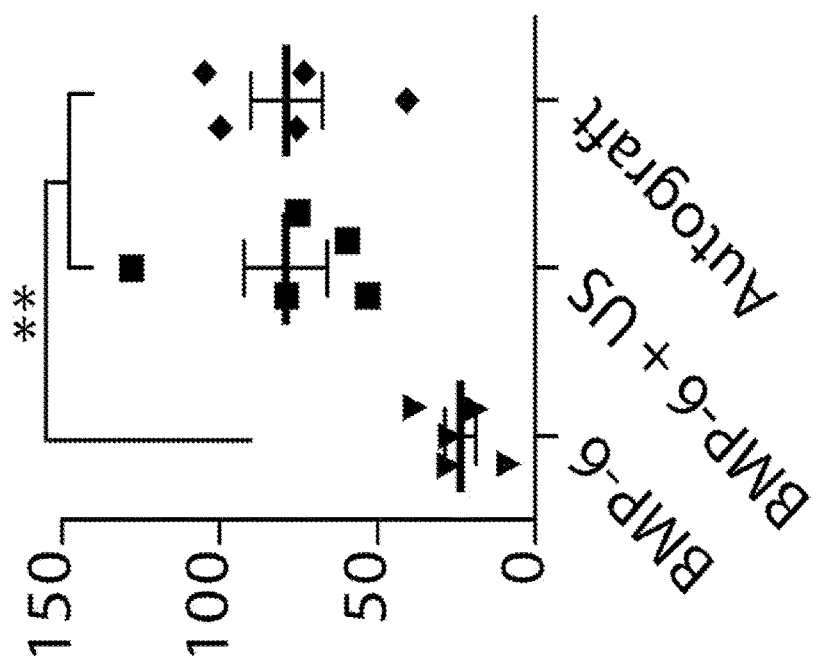

Figure 17
Fig. 17A
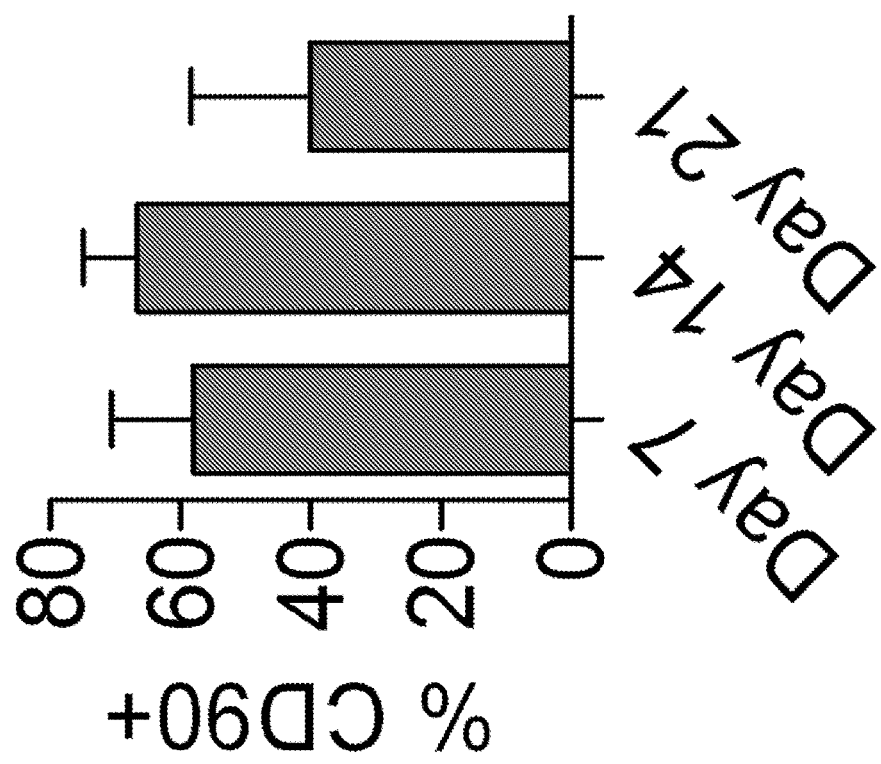
Fig. 17B
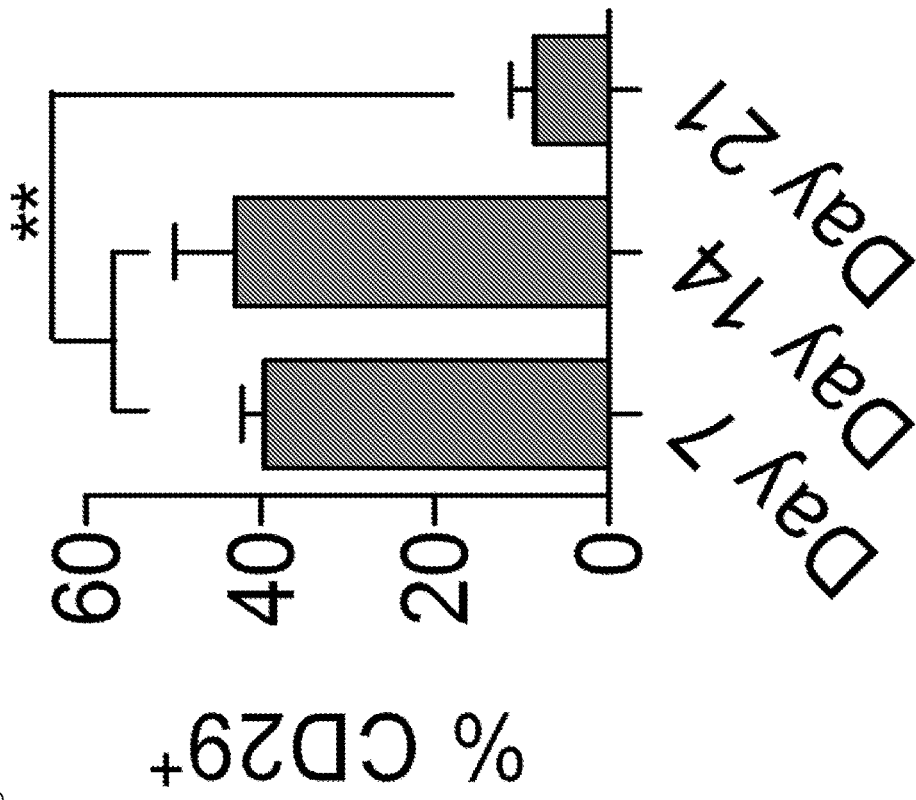

METHOD OF ENDOGENOUS STEM CELL ACTIVATION FOR TENDON/LIGAMENT OSSEOINTEGRATION

CROSS-REFERENCE TO RELATED APPLICATIONS

This application is a National Phase of International Application No. PCT/US2017/020033, filed Feb. 28, 2017, which designated the U.S. and that International Application was published under PCT Article 21(2) in English. This application claims priority under 35 U.S.C. § 119(e) to U.S. Provisional Application No. 62/301,176, filed Feb. 29, 2016, the contents of which are herein incorporated by reference in their entirety.

STATEMENT REGARDING FEDERALLY SPONSORED RESEARCH OR DEVELOPMENT

This invention was made with government support under Grant No. TR000124, awarded by The National Institutes of Health. The government has certain rights in the invention.

FIELD OF THE INVENTION

Described herein are methods and compositions related to therapies for bone, tendon and ligament repair by enhanced gene delivery using ultrasound.

BACKGROUND

Tendon and ligament injuries are common in orthopaedic clinical practice and cause substantial morbidity in sports and in routine daily activities. The anterior cruciate ligament (ACL) of the knee and the rotator cuff of the shoulder are included among the most commonly injured soft-tissue structures. Surgical reconstruction has been the gold standard treatment option for tendon and ligament injuries, in which a tendon auto- or allograft is implanted and attached to the bone. Although surgeons have been able to reconstruct ligaments such as the ACL with predictable success, the integrity of these reconstructions still depends on adequate biological healing of the interface between ligament and bone. Healing of this interface is a slow process that often times results in the formation of fibrotic reparative tissue bridging the gap between these two tissue types.

Unfortunately, when these ligaments are reconstructed surgically, the majority of patients suffer from a prolonged period of recovery (up to 1-year). Achieving tendon/ligament-to-bone healing that is functionally and biologically similar to native anatomy can be challenging because of the limited regeneration capacity of the tendon-bone interface. Several biological approaches have been proposed to enhance ligament-bone integration. These strategies include the delivery of osteoinductive growth factors, platelet rich plasma, viral transduction of genes encoding growth factors, and cell based therapies. Although there were some promising results, all of these strategies have disadvantages: growth factors need to be injected repeatedly due to short half-life, viral vectors can be hazardous for use in humans and implantable cell therapies require complex ex vivo manipulation. Furthermore, growth factors can be very expensive and cell-based therapies would likely necessitate a prolonged regulatory process by the USFDA. In light of these obstacles, there is a great need in the art for a new and improved biological therapy to enhance bone-allograft integration.

Previously, the Inventors developed a procedure first involving surgical implantation of a biodegradable scaffold in order to recruit endogenous stem cells to an injury site and an ultrasonic pulse is used to facilitate percutaneous delivery of an osteogenic gene to the recruited cells. This approach proved to be very successful and resulted in complete bone regeneration in critical size bone defects in a pig model. These successful results utilizing this procedure in order to enhance allograft bone integration for ACL reconstruction provide a solid foundation for facilitating healing.

Described herein is the discovery that that targeted bone morphogenic protein (BMP) gene delivery to resident stem cells will enhance tendon allograft integration into bone in a large animal model. The proposed therapy was applied on the bone-allograft enthesis site in a pig's knee ACL reconstruction model. Using a ultrasound based gene delivery in a pig model of ACL reconstruction, tendon allograft bone integration in a pig model was improved using targeted BMP gene delivery to endogenous stem cells. As endogenous mesenchymal stem cells (MSCs) can be recruited to bone injury sites using a collagen scaffold, ultrasound-based BMP gene delivery is shown as capable of further promoting bone regeneration. Transient expression of a BMP transgene is sufficient for efficient local bone regeneration and ultrasound-based gene delivery to ACL reconstruction bone tunnels provides a significant new advance in orthopaedic treatment.

BRIEF DESCRIPTION OF THE FIGURES

FIG. 3: Reporter gene expression in mini-pigs' tibia bone defects following ultrasound-mediated gene delivery. FIG. 3A—40-50% of the cells expressed GFP (n=3-4, p<0.05) (US=ultrasound). FIG. 3B—70-90% of the cells transfected with GFP, were endogenous MSCs. Cells isolated from bone defects were analyzed using flow cytometry for co-expression of GFP and MSC markers (CD 90, 29 and 44) (n=3-4, =p<0.01, *=p<0.001).

FIG. 4: Ultrasound-mediated BMP-6 gene delivery to pig tibia bone defect induces complete defect repair. 1 cm bone defect was created in mini-pigs' tibiae and implanted with collagen scaffolds (FIG. 4A—fluoroscopic image shows defect and fixation plate; Arrow indicates bone defect). On Day 14 post surgery, BMP-6 plasmid was injected to the defect site followed by an ultrasonic pulse. 6 weeks post gene delivery animals were sacrificed. MicroCT quantitative analysis demonstrated significantly more bone volume (FIG. 4B) and bone density (FIG. 4C) in tibia defects treated with BMP-6 compared to defects treated with BMP-2 or controls. Normal intact tibiae were used as controls. MicroCT images showed complete healing of BMP-6 treated bone defects (FIG. 4D). (–p<0.01; *–p<0.001; ****–p<0.0001). [MBs=microbubbles, US=ultrasound].

FIG. 5: BMP-6 treated pig tibiae show superior biomechanical properties. Torsional testing was performed to examine the mechanical properties of the treated tibial defects 8 weeks after surgery. Tibial defects treated with BMP-6 and ultrasound showed significantly higher stiffness, strength and toughness compared with tibial defects treated with BMP-2 and ultrasound ("BMP-2+US" group) or BMP-6 plasmid alone ("Plasmid only" group). Normal intact tibiae were used as controls. (*–p<0.05; –p<0.01; *–p<0.001; ****–p<0.0001)

FIG. 6: Mini pig ACL reconstruction model demonstrating ligaments, bone structures, and reconstruction as described in the application.

FIG. 7: Ultrasound-mediated transgene delivery to endogenous MSCs in ACL reconstruction bone tunnels. A porcine tendon allograft was used to reconstruct a pig's ACL. 14 days later, GFP plasmid was injected to bone tunnels under fluoroscopic guidance followed by ultrasound application to the femoral tunnel (FIG. 7A, FIG. 7B). FACS analysis done 5 days post gene delivery showed that 50% of the cells in the femoral tunnel expressed GFP (FIG. 7C). In addition 12-22% of the cells in the tunnels expressed MSC markers (FIG. 7D) (n=3, *=p<0.05). [US=ultrasound]

FIG. 8: Ultrasound-mediated BMP-2 gene delivery to endogenous MSCs in ACL reconstruction bone tunnels. FIG. 8A, FIG. 8B—Quantification of bone volume and apparent density in the tibial and femoral tunnels showing significant higher values in the femoral tunnel (n=3; *p<0.05, t-test). FIG. 8C, FIG. 8D—Representative microCt images of the bone tunnels. FIG. 8E, FIG. 8F—MRI scans of mini-pig's knee joint showing the femoral (FIG. 8E) and tibial (FIG. 8F) tunnels.

FIG. 9: Ultrasound-mediated BMP-6 gene delivery to endogenous MSCs in ACL reconstruction bone tunnels. A—Quantification of bone volume in tunnels showing significantly higher values in BMP-6 treated animals (n=6; *p<0.05, t-test). B, C—Representative microCT images of BMP-6 treated and untreated femoral bone tunnels. D-Fluoroscopic 3D reconstruction of a representative treated animal demonstrating no ectopic bone formation around treated bone tunnels.

FIG. 10: BMP-6 treated ACL reconstruction pigs show superior biomechanical properties. FIG. 8A—AP laxities at ±20N of BMP-6+US treated pigs were lower than untreated pigs. The linear stiffness (FIG. 8B) and Maximum load to failure (FIG. 8C) were both significantly higher than untreated pigs, showing stronger graft-bone integration in treated animals. (n=3; *p<0.05, t-test).

FIG. 11. Reporter gene expression in mini-pigs' tibial fractures following ultrasound-mediated gene delivery. (FIG. 11A) Ex-vivo fluorescent imaging of an exposed GFP-treated fracture, five days after treatment. Fracture margins are denoted by a dashed square. (FIG. 11B) Flow cytometry analysis of the percentage of GFP-positive cells isolated from fracture sites, with or without ultrasound treatment, five days after treatment. (FIG. 11C) Mean fluorescence intensity per cell isolated from fractures, with or without ultrasound treatment, five days post-treatment. (FIG. 11D) Luciferase enzyme activity in cells isolated from fracture sites, with or without ultrasound, five days after treatment. (FIG. 11E) CD29-, (FIG. 11F) CD90- and (FIG. 11G) CD44-positive cells out of GFP-positive cells isolated from the fractures, with or without ultrasound treatment, five days after treatment. ("No US" group: n=3, "US" group: n=4; *p<0.05, p<0.01, **p<0.0001; US=ultrasound, GFP=green fluorescent protein, RLU=relative light units).

FIG. 12. BMP-6 expression following ultrasound-mediated gene delivery to fracture site. (FIG. 12A) Gene (relative quantification (RQ)) and (FIG. 12B) protein expression in tibial fracture sites 2, 5 and 10 days after ultrasound-mediated BMP-6 gene delivery. (n=3 per experimental group; US=ultrasound; *p<0.05, p<0.01, **p<0.0001)

FIG. 13. Ultrasound-mediated BMP-6 gene delivery to mini-pigs' tibial bone fractures. Quantitative analysis of bone formation in the tibial fractures, including (FIG. 13A) bone volume density and (FIG. 13B) apparent density. (FIG. 13C) Representative μCT slices of the fractures, 8 weeks after surgery. Asterisks denote new bone formation within the fracture. Arrows point to cortical discontinuity indicating nonunion within the fracture. Autograft margins are denoted by a dashed square. (FIG. 13D) Masson's trichrome staining of tibial fractures, eight weeks post-surgery, at low magnification (upper subfigures) and high magnification of the yellow square (lower subfigures). Arrows point to the border between native bone and new-formed bone in the fracture. Scale bars, 1 mm. (US=ultrasound; Autograft: n=7; BMP-6+US: n=8; BMP-6 only: n=6; US only: n=3; Scaffold only: n=4; p<0.01, *p<0.001).

FIG. 14. Biomechanical properties of treated tibiae. Torsion testing was performed on harvested tibias. (FIG. 14A) A mounted tibia reaching its failure point. Analysis of load and rotation was performed to determine the (FIG. 14B) strength, (FIG. 14C) stiffness and (FIG. 14D) toughness of treated bones (US=ultrasound, N.m=Newton metre; n=5 per experimental group; *p<0.05, **p<0.01).

FIG. 15. Proposed therapy. Ultrasound-mediated microbubble-enhanced bone morphogenetic protein gene delivery induces rapid and efficient regeneration of a critical-sized bone fracture.

FIG. 16. Critical-size bone fracture model in Yucatan minipigs' tibia. (FIG. 16A) During surgery the tibia was exposed anteromedially and a fracture was created (denoted by white arrow) by removing 1 cm of bone from the diaphysis (shown in the right lower insert). The fractured bone was stabilized using a custom-made 6-hole limited-contact dynamic compression plate. (FIG. 16B) A postoperative fluoroscopic image of the stabilized tibial bone (arrow). (FIG. 16C) A micro-computed tomography scan of the fracture immediately following ultrasound application, 14 days after the surgery (fracture site denoted by dashed square).

FIG. 17. Endogenous mesenchymal progenitor cell recruitment to mini-pig tibial fracture site. Flow cytometry analysis of (FIG. 17A) CD29- and (FIG. 17B) CD90-positive cells from tibial fracture sites at 7, 14 and 21 days postoperatively (n=3 per time-point; **p<0.01) FIG. 18. Ultrasound treatment setup. (FIG. 18A) Fluoroscopic imaging of the fracture site. The needle is seen in the center of the fracture site. (FIG. 18B) Injection of a DNA and microbubble mixture into the fracture site. The ultrasound probe is placed adjacent to the needle for optimal visualization of the injected mixture. (FIG. 18C) Ultrasound B-mode visualization of the fracture site (marked by a yellow dashed square). The cortex of the tibia bone is marked by a red dashed line. (FIG. 18D) Ultrasound contrast agent imaging of the fracture site (yellow dashed square) during DNA and microbubbles injection. The cortex of the tibia bone is marked by a red dashed line.

FIG. 19. Biodistribution of BMP-6 expression following ultrasound-mediated gene delivery. BMP-6 gene expression in various organs two and ten days after ultrasound-mediated BMP-6 treatment, compared to untreated animals. (BM=bone marrow; n=3 per time-point).

SUMMARY OF THE INVENTION

Figure 1:
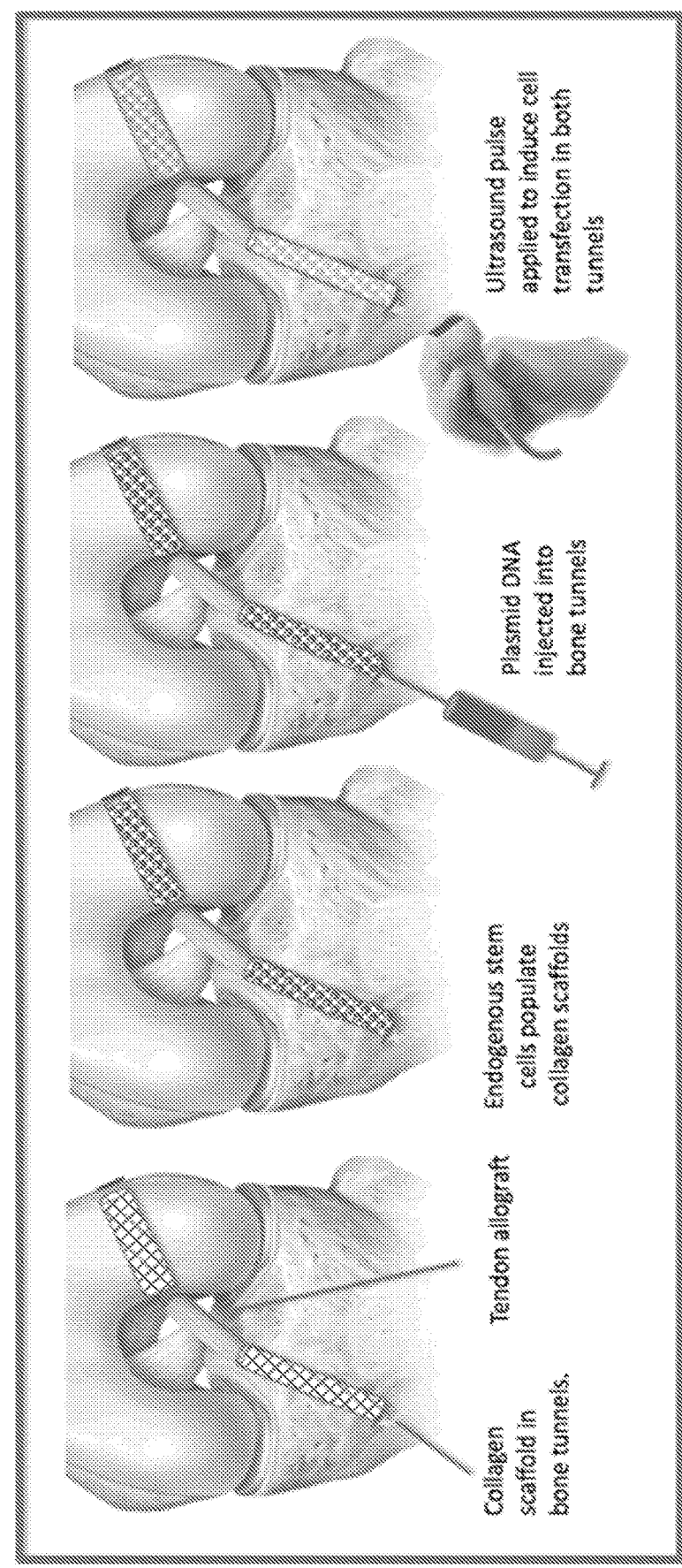
FIG. 1: A two-step procedure that leads to accelerated tendon/ligament integration to bone. In the first step endogenous stem cells are recruited to the site of tendon/ligament-bone interface and in the 2nd step, an osteogenic gene is delivered to the recruited stem cells with the aid of ultrasound.

Described herein is a method of promoting osseointegration, including administering an agent at a tissue site including interface of: (i) bone and (ii) tendon or ligament and delivering one or more vectors encoding one or more proteins at the tissue site, wherein cells at the tissue site express the one or more proteins, thereby promoting osseointegration. In other embodiments, the agent is capable of recruiting stem cells to the tissue site. In other embodiments, the the agent is a scaffold. In other embodiments, the scaffold includes collagen. In other embodiments, the tissue site includes one or more bone tunnels. In other embodiments, delivering one or more vectors includes injection. In other embodiments, delivering one or more vectors includes ultrasound. In other embodiments, the one or more proteins comprise bone morphogenic proteins (BMPs). In other embodiments, the BMPs comprise bone morphogenic protein-6 (BMP-6). In other embodiments, the BMPs comprise bone morphogenic protein-2 (BMP-2). In other embodiments, wherein osseointegration is measured using computer tomography (CT) scan. In other embodiments, osseointegration is measured using magnetic resonance (MR) imaging. In other embodiments, the tissue site includes injured tissue. In other embodiments, injured tissue includes anterior cruciate ligament, posterior cruciate ligament, medial collateral ligament of the knee and elbow, lateral collateral ligament of the knee and elbow, and rotator cuff tendon tears. In other embodiments, the injured tissue has been reconstructed. In other embodiments, the reconstruction includes an autograft and/or allograft.

Also described herein is a kit including a biodegradable agent, one or more vectors encoding one or more proteins, a microbubble solution, and instructions for use In other embodiments, the agent is capable of recruiting stem cells to the tissue site. In other embodiments, the agent is a scaffold. In other embodiments, the scaffold includes collagen. In other embodiments, the one or more proteins comprise bone morphogenic proteins (BMPs). In other embodiments, the BMPs comprise bone morphogenic protein-6 (BMP-6). In other embodiments, the BMPs comprise bone morphogenic protein-2 (BMP-2).

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual 4th ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Tendon and ligament injuries are common in orthopaedic clinical practice and cause substantial morbidity in sports and in routine daily activities. The ACL and rotator cuff are included among the most commonly injured soft-tissue structures. Rotator cuff ruptures are the most common degenerative tendon injury and occur mainly in older patients as multifactorial disorders manifesting the main symptoms of pain and restricted range of motion. Although the precise prevalence of symptomatic rotator cuff injuries is unknown, it may range from 5% to 30%. In cadaver studies of elderly donors, the prevalence of full-thickness tears has been estimated to be as high as 30%. Rotator cuff repair is one of the most common orthopaedic procedures and perhaps the most common of all shoulder surgeries. Between 200,000 and 300,000 rotator cuffs are surgically repaired each year, with a 15-20% failure rate. The ACL is the most important stabilizer of physiological knee motion. ACL injuries have an annual incidence of more than 200,000 cases in the United States alone, with ~100,000 of these knees reconstructed annually. ACL injury is most prevalent (1 in 1,750 persons) in patients 15-45 years of age. It is more common in this age group in part because of their more active lifestyle as well as higher participation in sports. Athletes who participate in high demand sports like soccer, football, and basketball are more likely to injure their ACL. An ACL injury can be devastating, particularly for a young athlete where high-level participation in strenuous sports is often not possible without surgical reconstruction of the ACL. Furthermore, the long-term development of knee osteoarthritis (OA) is common. Recent study with 12-year follow-up showed that about 50% of patients following ACL reconstruction surgery developed OA. The mean age of patients at follow-up was 31 years. At this age, there are no good treatment options for a symptomatic osteoarthritic knee. It is therefore important to develop new approaches for tendon-to-bone healing, aiming to maintain both long-term health and quality of life.

Surgical reconstruction has been the gold standard treatment option for tendon and ligament injuries. During this procedure, an autologous or allogeneic tendon is implanted to replace the damaged ligament. Successful tendon-to-bone healing is critical to restore function and stability of the joint. However, this healing process occurs slowly and in some cases incompletely, leading to poor graft-bone integration those results in structural instabilities and morbidities. During the past decade, strategies to biologically accelerate and improve tendon-to-bone healing have been studied using growth factors and cell-based therapies. These strategies include the delivery of osteoinductive growth factors, platelet rich plasma, viral transduction of genes encoding to growth factors, and cell based therapies. In particular, bone morphogenic proteins (BMPs) were studied to enhance integration of tendons in the bone tunnels. However, BMPs are extremely costly and have recently been heavily scrutinized for a high incidence of side effects, possibly due to their use in megadoses.

The tendon-to-bone junction is slow to heal because of the relative avascularity of the fibrocartilage zone and bone loss at the site of injury. To overcome this challenging environment, osteoprogenitor cells (mainly mesenchymal stem cells (MSCs)), combined with growth factors (mostly BMPs), can be used as potent bone inducers in order achieve better enthesis and improved tendon-to-bone healing. In a series of publications, the Inventors showed that MSCs engineered to overexpress different BMP genes can differentiate and contribute to the process of bone formation in vivo, leading to complete regeneration of segmental defects. However, such an approach requires several steps—cell isolation, expansion, and engineering—which complicates and prolongs the regulatory pathway to clinical use. An alternative targeted gene therapy approach would be to overexpress an osteogenic gene, such as a BMP, in MSCs residing at the enthesis site. This is an attractive approach because it results in a transient secretion of the BMP protein at physiological levels and it does not require harvesting of cells or grafts, or the production of high-cost reagents such as recombinant proteins. Yet the efficiency of gene expression strongly correlates with the vector carrying the gene to the target site. A wide array of gene delivery methods have been developed and tested for bone regeneration over the years. There is no doubt that viral vectors are the most efficient gene delivery tools, but their efficiency is offset by potential risks of tumorigenic and immunogenic reactions. Nonviral vectors are considered safer for human use, albeit much less efficient for gene expression. To enhance the efficiency of in vivo nonviral gene delivery, methods that rely on a short pulse of energy were developed. These methods induce the formation of transient nano-sized pores in the membranes of cells, enabling the uptake of DNA, which leads to cell transfection. Cell poration can be induced by an electric pulse, ultrasound, or laser energy.

Ultrasound is widely used in the clinic for diverse purposes such as imaging, lithotripsy, and tumor ablation. Preclinical studies have been conducted to investigate the possibility of ultrasound-mediated gene therapy. This delivery method, called sonoporation, is an attractive approach because it results in transient gene expression and does not require potentially tumorigenic and immunogenic viral vectors or invasive electroporation. Since ultrasound application can be localized to a region of interest, deep tissues can be specifically sonoporated with minimal systemic effects. Most sonoporation studies have combined plasmid DNA with microbubbles (MBs) in order to enhance membrane permeability via the effects of microbubble volume fluctuations and/or collapse. Indeed, previous attempts have shown the feasibility of inducing bone formation using in vivo cell poration and direct delivery of plasmids encoding for a BMP gene. However, none of these studies were performed in a site of bone injury.

There is a great need in the art for a new and improved biological therapy aimed at addressing the current unmet clinical need in the treatment of ligament and tendon injuries. The anterior cruciate ligament (ACL) injury of the knee will can serve as an excellent experimental model. It has been reported that at least 100,000-200,000 ACL reconstructions are performed in the US each year. ACL reconstruction, like all knee ligament reconstructions, requires the implantation of autologous or allogeneic tissue into bone tunnels drilled at the tibia and femur. Unfortunately, when these ligaments are reconstructed surgically, it is not uncommon for many of these patients to endure a prolonged period of rehabilitation (up to approximately one year). One critical factor, especially in the setting of soft-tissue graft reconstructions, is the adequate and timely integration of the graft at the tendon-bone interface. The biology of ACL graft integration into host bone is the main tenet that guides early rehabilitation exercise restrictions. Furthermore, it is known that the incorporation of allograft ACL reconstructions is delayed in comparison to autograft reconstructions. The American Orthopaedic Society for Sports Medicine (AOSSM) has estimated that approximately 60,000 allografts were used in knee reconstruction procedures alone in 2005. In light of this, the development of new therapeutic interventions with an ability to accelerate graft integration would have a tremendous clinical impact, and, in turn, these interventions could translate into patients experiencing a more rapid return to unrestricted activities.

Several biological approaches have been proposed to enhance ligament-bone integration. These strategies include the delivery of osteoinductive growth factors, platelet rich plasma, viral transduction of genes encoding growth factors, and cell based therapies. For example, some studies have reported delivery of viral vectors to the ligament/tendon-bone interface, encoding bone morphogenetic protein (BMP) or cyclooxygenase 2. In some instances, a two-step procedure in which the injection of recombinant human BMP into a tendon autograft induced ectopic bone formation, serves as an experimental enthesis in a ACL reconstruction model. Although there were some promising results, all of these strategies have a variety of disadvantages including: growth factors needing to be injected repeatedly due to their short half-life, viral vectors being potentially hazardous for use in humans and implantable cell therapies requiring complex ex vivo manipulation. Furthermore, recombinant proteins can be very expensive and cell-based therapies would likely necessitate a prolonged regulatory and approval process by the USFDA.

An attractive alternative would be non-viral delivery of osteogenic genes to the site of the ligament-bone junction. Unfortunately, viral vectors are much more efficient than most non-viral methods. To enhance the efficiency of in vivo non-viral gene delivery, methods have been developed that rely on a short pulse of energy to optimize gene delivery. These methods induce the formation of transient nano-sized pores in the membranes of cells, enabling the uptake of DNA, which leads to cell transfection. This cell poration can be induced by an electric pulse, ultrasound, or laser energy.

The Inventors' group has studied the potential of targeted ultrasound-mediated gene delivery to endogenous stem cells. Using a two-step procedure where the Inventors first implant a biodegradable scaffold into a bone defect in order to recruit endogenous stem cells to the injury site. This is then followed by the administration of a short pulse of energy (either electrical or ultrasonic) to deliver the Inventors' gene of interest into the recruited cells. This approach results in targeted bone regeneration in a rodent model. The Inventors have shown that host progenitor cells migrate to the site of scaffold implantation and then subsequently become the target for transgene delivery at the specified location. Next the Inventors were able to show that a similar approach has led to complete bone defect regeneration in a mini-pig tibia model.

Such results represent the first successful demonstration of targeting bone formation at an injury site using ultrasound-mediated gene delivery. This method has several advantages: 1. It leads to accelerated bone formation at a specific location and thus could enhance ligament-bone integration; 2. It does not require repeated delivery of costly growth factors such as recombinant BMP; 3. It does not require stem cell manipulation ex vivo; 4. It translates easily to the clinical setting, as it requires an ultrasound system which is already widely used clinically; 5. The technology is safe and requires only a transient expression of the transgene in order to induce bone formation (no viral vectors or sustained integration of DNA are required).

The proposed therapeutic approach has great potential for the enhancement of ligament/tendon integration into bone. The biology behind the proposed treatment has been demonstrated, with a particular focus on the role of endogenous progenitor cells without ex vivo manipulation. Thus, the next logical application of this technology is in a large animal model serving as a precursor to human clinical trials. Given that ultrasound technology is widely integrated into routine patient care, the Inventors believe that this project will easily translate into clinical practice. It should be noted that the localized endogenous guided differentiation described here is applicable to all ligament/tendon reconstructions, including multi ligamentous knee injuries and rotator cuff tendon repairs, which continue to be associated with a high rate of recurrent tearing despite modern repair techniques.

One can promote complete repair of segmental bone defects by direct BMP transfection to endogenous MSCs using in vivo cell poration. Endogenous stem cells can be recruited to the defect site using the implantation of a collagen scaffold and can be targeted for gene delivery. Further, ultrasound can be used in the same manner for delivering genes of interest into bone voids and fracture sites. Finally, this ultrasound approach can be used to completely heal a segmental bone fracture in a large animal model. Combining these features, a two-step procedure can lead to accelerated tendon/ligament integration to bone. In the first step endogenous stem cells are recruited to the site of tendon/ligament-bone interface and in the 2nd step, an osteogenic gene is delivered to the recruited stem cells with the aid of ultrasound. These features combined together can establish an approach for enhancing graft-bone integration, restored function and control following tendon reconstruction surgery. The use of stem cells, ultrasound, and gene delivery in combination can provide a significant number of benefits to a wide variety of patients suffering from soft-tissue structure injuries in the musculoskeletal system.

Described herein is a method of promoting osseointegration, including administering an agent at a tissue site including interface of: (i) bone and (ii) tendon or ligament, and delivering one or more vectors encoding one or more proteins at the tissue site, wherein cells at the tissue site express the one or more proteins, thereby promoting osseointegration. In other embodiments, the agent is capable of recruiting stem cells to the tissue site. In other embodiments, the agent is a scaffold. In other embodiments, the scaffold includes collagen. For example, the collagen scaffold will be implanted at the bone tunnel. In other embodiments, the tissue site includes one or more bone tunnels. In other embodiments, delivering one or more vectors includes injection. In other embodiments, delivering one or more vectors includes ultrasound. In various embodiments, the one or more vectors, including DNA vectors such as plasmids, are mixed with microbubbles. For example, in some embodiments, delivering vectors could include, one injection of up to 1 mg of bone morphogenic protein (BMP) encoding plasmid suspended in $10^7$ microbubbles. In other embodiments, the quantity of plasmid includes about 0.1-0.25 mg, about 0.25-0.50 mg, about 0.5-1.0 mg, about 1.0-1.5 mg, about 1.5-2.0 mg or 2 mg or more. In other embodiments, the quantity if plasmid is suspended in $10^5$, $10^6$, $10^7$, $10^8$ or more microbubbles. In other embodiments, the BMP plasmid should yield the secretion of nanograms of protein per day over a period of two weeks. In various embodiments, delivering one or more vectors can include multiple administration. For example, optional repeat courses of therapy within 3 to 6 months following demonstration of a partial response based on imaging and functional improvements. In other embodiments, the ultrasonic pulse will be applied in a transcutaneous manner. In other embodiments, the one or more proteins comprise bone morphogenic proteins (BMPs). In other embodiments, the BMPs comprise bone morphogenic protein-6 (BMP-6). In other embodiments, the BMPs comprise bone morphogenic protein-2 (BMP-2). In other embodiments, osseointegration is measured using computer tomography (CT) scan. In other embodiments, osseointegration is measured using magnetic resonance (MR) imaging. For example, osseointegration and improvements in osseointegration can be measured by observing an increase the rate new bone formation at bone tunnel site as demonstrated by CT scan, and increase in bone volume and density at the bone tunnel sites as demonstrated by MR imaging, or an increase the rate of graft integration to bone as compared to standard care without abnormal or excessive bone formation. In other embodiments the tissue site includes injured tissue. In other embodiments, injured tissue includes anterior cruciate ligament, posterior cruciate ligament, medial collateral ligament of the knee and elbow, lateral collateral ligament of the knee and elbow, rotator cuff tendon tears. In other embodiments, the injured tissue has been reconstructed. In other embodiments, the reconstruction includes an autograft and/or allograft. A variety of endpoints can demonstrate improved osseointegration as associated with reconstructive surgery. For example, in knee ligament reconstructions: The proportion of patients who are able to return to playing sports involving cutting and pivoting activities earlier than controls. The Inventors sill also assess improvement in patient-reported outcome scores (according to Tegner Activity Level Scale and Marx Activity Scale. This will include stratifying results by the graft source (anatomic donor site) used for the reconstruction as well as whether the graft is allogeneic or not. The proportion of patients who experience recurrent knee ligament injury. The proportion of patients with the ability to perform single limb agility exercises using the affected extremity to a level that is 80% or greater of the value measured for the same tasks performed with the contralateral uninjured extremity (ex. Single leg hop testing, Y-balance testing, functional movement screen). Alternatively, in rotator cuff tendon repairs: The Inventors will assess improvement in patient-reported outcome scores (American Shoulder and Elbow Society Shoulder Assessment score), objective manual motor strength testing and active range of motion testing. In such instances, criteria for demonstrating efficacy can include a measurement of the proportion of patients who are able to return to activities involving cutting and pivoting earlier than controls. Alternatively, one can measure the proportion of patients who are able to resume activities of daily living without significant pain, weakness or range of motion limitations.

Described herein is a method of bone fracture repair including delivering one or more vectors encoding one or more proteins at a bone fracture site, wherein cells at the fracture site express the one or more proteins, thereby promoting repair of the bone fracture. In other embodiments, an agent is administered at the bone fracture site before delivering the one or more vectors. In other embodiments, the agent is capable of recruiting stem cells to the tissue site. In other embodiments, the agent is a scaffold. In other embodiments, the scaffold includes collagen.

In other embodiments, delivering one or more vectors includes injection. In other embodiments, delivering one or more vectors includes ultrasound. In various embodiments, the one or more vectors, including DNA vectors such as plasmids, are mixed with microbubbles. For example, in some embodiments, delivering vectors could include, one injection of up to 1 mg of bone morphogenic protein (BMP) encoding plasmid suspended in $10^7$ microbubbles. In other embodiments, the quantity of plasmid includes about 0.1-0.25 mg, about 0.25-0.50 mg, about 0.5-1.0 mg, about 1.0-1.5 mg, about 1.5-2.0 mg or 2 mg or more. In other embodiments, the quantity of plasmid is suspended in $10^5$, $10^6$, $10^7$, $10^8$ or more microbubbles. In other embodiments, the BMP plasmid should yield the secretion of nanograms of protein per day over a period of two weeks. In various embodiments, delivering one or more vectors can include multiple administration. For example, optional repeat courses of therapy within 3 to 6 months following demonstration of a partial response based on imaging and functional improvements. In other embodiments, the ultrasonic pulse will be applied in a transcutaneous manner. In other embodiments, the one or more proteins comprise bone morphogenic proteins (BMPs). In other embodiments, the BMPs comprise bone morphogenic protein-6 (BMP-6). In other embodiments, the BMPs comprise bone morphogenic protein-2 (BMP-2).

In other embodiments, the bone fracture repair is a fracture suitable for treatment with a graft. This includes, for example, bone grafts including a gap greater than 1 cm. This further includes long bones such as tibia, fibula, femur but also other bones such as mandible, craniofacial bones, and spine.

Described herein is a method of enhancing gene delivery at a tissue site. In various embodiments, the method includes delivering one or more vectors encoding one or more proteins at a tissue site, wherein delivery includes ultrasound and imaging of microbubbles and continued application of ultrasound until a substantial majority of microbubbles have dissipated, thereby enhancing gene delivery at the tissue site. In other embodiments, an agent is administered at the bone fracture site before delivering the one or more vectors. In other embodiments, the agent is capable of recruiting stem cells to the tissue site. In other embodiments, the agent is a scaffold. In other embodiments, the scaffold includes collagen.

In other embodiments, delivering one or more vectors includes injection. In various embodiments, the one or more vectors can be in a mixture with microbubbles, including DNA vectors such as plasmids. For example, a mixture of DNA and microbubbles is injected while being imaged using an ultrasound unit. In various embodiments, ultrasonic pulse is applied to dissipate a substantial majority of microbubbles, wherein a substantial majority includes greater than 50%, 60%, 70%, 80%, 90% or more of the microbubbles. In various embodiments, ultrasound includes ultrasonic pulse with a transmission frequency of about 1.0, 1.1, 1.2, 1.3, 1.4, 1.5 MHz. In various embodiments, ultrasound includes mechanical index of about 0.3, 0.4, 0.5, 0.6, 0.7, 0.8, 0.9. In various embodiments, ultrasound includes a depth of about 1, 2, 3, 4, 5, 6, 7 or 8 cm. In various embodiments, ultrasound includes application for about 30-60 sec, about 1 minute to 2 minutes, 2-3 minutes, 3-4 minutes, and 4-5 minutes. In various embodiments, ultrasound includes ultrasonic pulse with a transmission frequency of 1.3 MHz, mechanical index of 0.6, and a depth of 4 cm for approximately 2 minutes until all visualized microbubbles burst. In another example, the same parameters are applied with a mechanical index of 1.2 and depth of 3 cm. In various embodiments, enhancing gene delivery includes a 10%-20%, 20%-30%, 30-40%, 40%-50%, 50% or more improvement in expression compared to a technique that that does not include imaging of microbubbles and continued application of ultrasound.

Example 1

Generally

Earlier studies have demonstrated the feasibility of osteoinduction using in vivo cell poration and direct delivery of plasmids encoding for a BMP gene. However, none of these studies were performed at a site of bone injury. The Inventors' prior studies have established that a segmental bone defect can be completely repaired by direct BMP transfection using cell poration.

Figure 2:
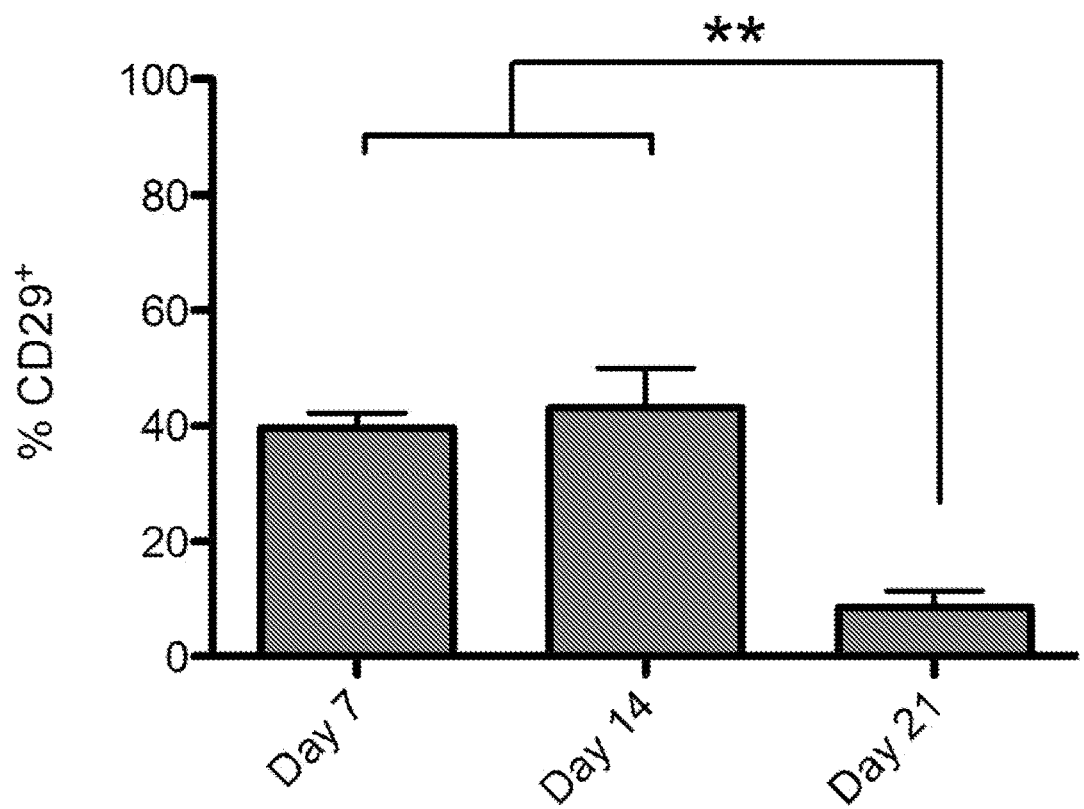
FIG. 2: Endogenous MSC recruitment to mini-pig tibia bone defect site. A 1-cm segmental defect was created in mini-pigs' tibiae and a collagen scaffold was implanted. 14 days later, a GFP plasmid was injected with microbubbles (MBs) to the defect site followed by an ultrasonic energy pulse. 5 days later cells were isolated from the defect site and were subjected to flow cytometry. The Inventors' results show that about 50% of the cells expressed MSC markers. Day 14 was selected as the target day for gene delivery since the percentage of marker expression decreased on Day 21 (n=3 per time point; p=0.0031).
Figure 2:
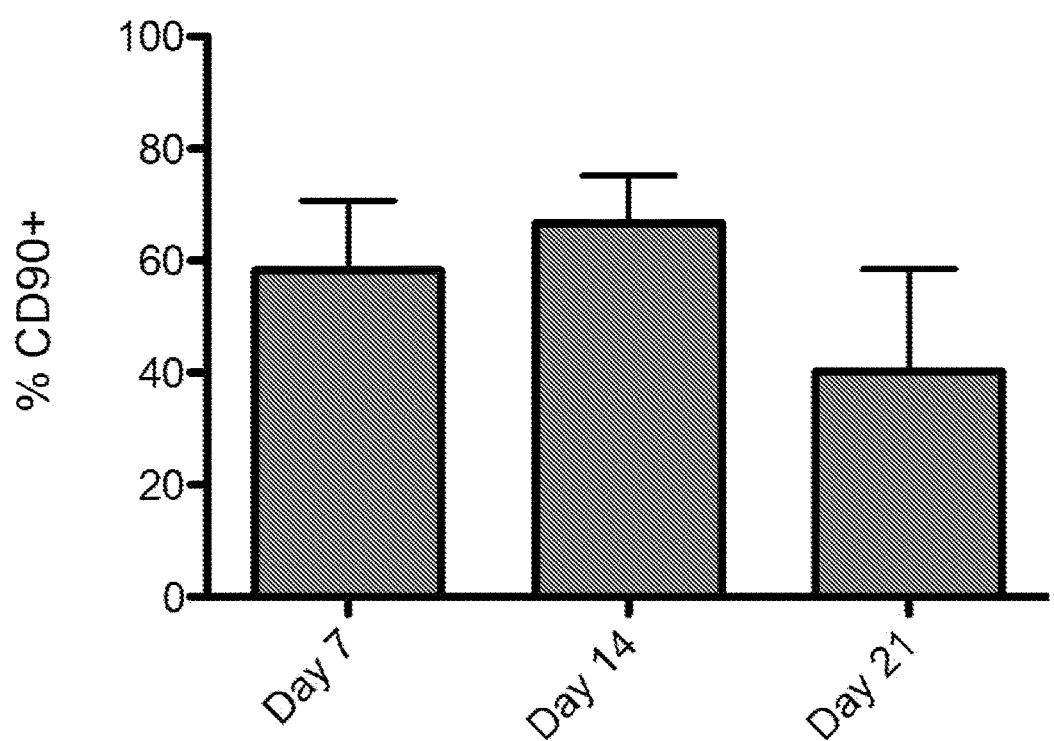

Without being bound by any particular theory, it is suggested here that to achieve efficient, targeted, bone regeneration non-viral gene delivery, this should be coordinated with the presence of endogenous mesenchymal stem cells (MSCs) at the defect site. For this purpose, a collagen scaffold was implanted at the bone defect site. Next, the Inventors analyzed cells that invaded and populated the scaffold at different time points after scaffold implantation. After 10 days (in a rat model) and 14 days (in a pig model) after scaffold implantation, the sponge was substantially invaded by host progenitors (see also FIGS. 1-2). At the second step the Inventors attempted to deliver a reporter gene, mixed in microbubbles (MBs) to enhance transfection efficiency, to the progenitors that migrated to the site of bone defect. Luciferase or GFP plasmids were injected, under fluoroscopic guidance, to bone defects created in rats' vertebrae and in a mini-pigs' tibiae. The Inventors used in vivo bioluminescence imaging to monitor transgene expression in the treated rats. Flow cytometry was used to quantify the percentage of cells that were transfected with GFP at the pigs' tibia bone defects. The Inventors' results showed that Luciferase expression was detected up to Day 35 post treatment and then decayed completely. This transient nature of transgene expression is advantageous, because it reduces the risk of ectopic or excessive growth of the target tissue type and because sustained transduction would present significant regulatory challenges for eventual human clinical trials.

Example 2

Detection of Cells Expressing In Vivo Delivered Transgenes

Figures 3, 3A:
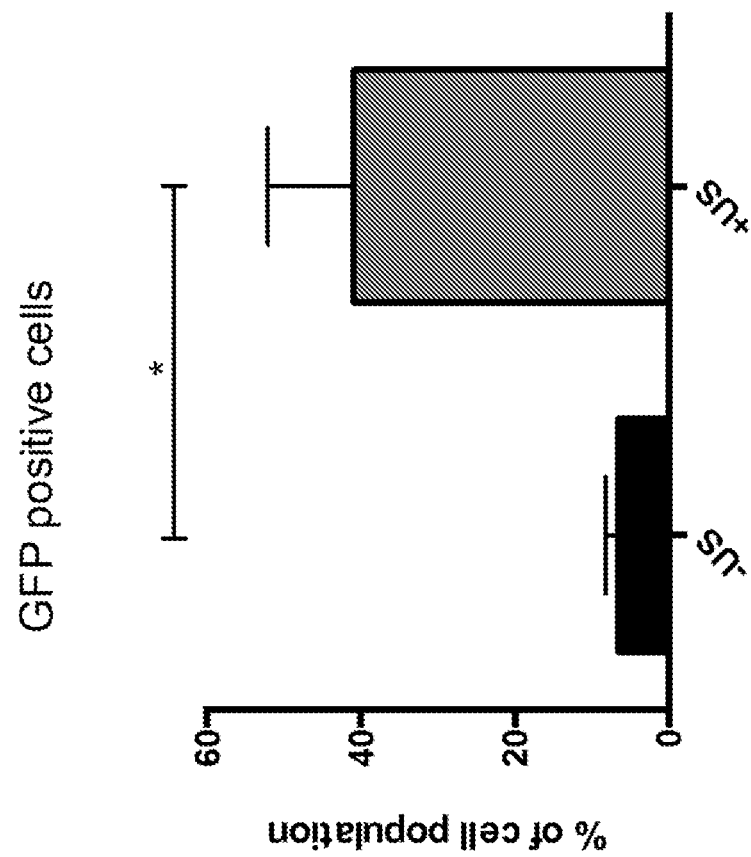
Figures 3, 3B:
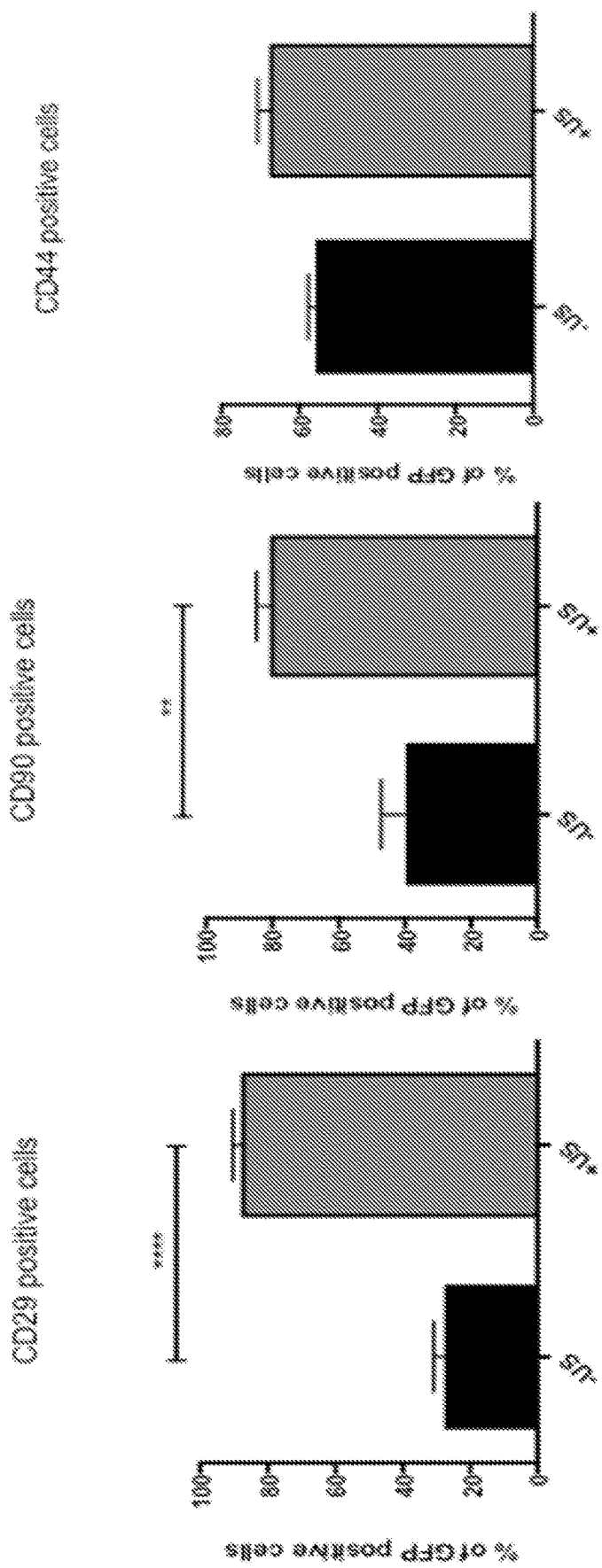

In the mini-pig tibial defect model the Inventors could show that 40-50% of the cells within the bone defect expressed GFP, 5 days post treatment (FIG. 3A). Moreover, the Inventors' flow cytometry results indicated that 70% of the transfected cells expressed known MSC markers (FIG. 3B).

Example 3

Bone Morphogenic Proteins (BMPs) as Promoting Bone Regeneration

Figures 4, 4D:
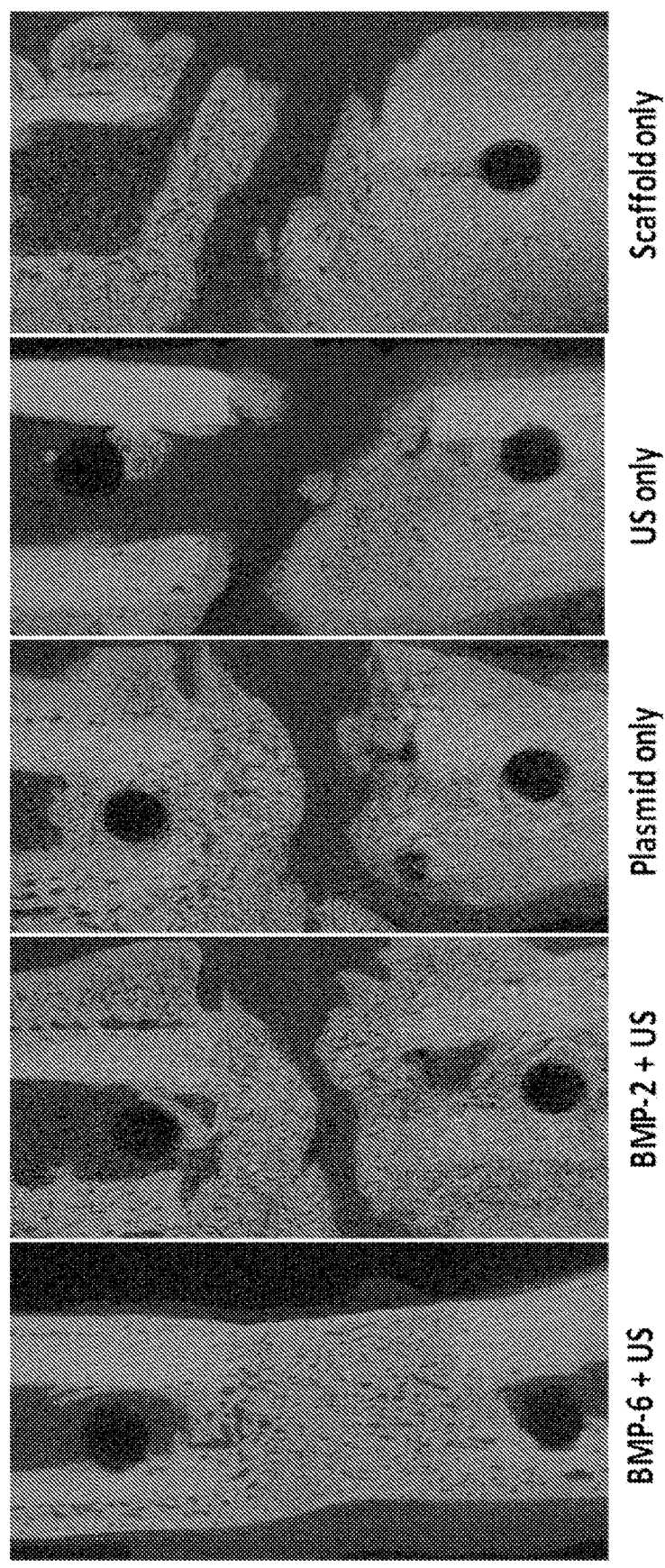

Using the mini-pig bone defect model described above, the Inventors attempted to deliver a gene encoding to BMP proteins in order to induce bone regeneration (FIG. 4). The Inventors used either BMP-2 or BMP-6 to evaluate their efficacy in bone regeneration, based on related studies showing that BMP-6 overexpression in MSCs leads to accelerated bone formation in vivo. As previously described, a first step included implanting a collagen scaffold in a 1 cm tibia segmental defect. Fourteen days later the Inventors injected 1 mg of plasmid DNA encoding for either BMP-6 ("BMP-6+US" group) or BMP-2 ("BMP-2+US" group) premixed with MBs. Next, the Inventors applied an ultrasonic pulse to the defect region, transcutaneously, using a clinical ultrasound machine (Sonos 5500, Phillips). To properly evaluate the synergistic effect of BMP genes and ultrasound, the following control groups were used: Injection of BMP-6 plasmid premixed with MBs alone ("Plasmid only" group); Injection of an empty plasmid vector premixed with MBs and exposure to ultrasound ("US only" group); and non-treated pigs who have only undergone the surgical procedure ("Scaffold only" group). These groups were also compared to their contralateral tibiae that remained intact. Eight weeks post defect formation (six weeks post treatment) the pigs were sacrificed and microCT analysis was used to quantify bone formation at the defect site. The results demonstrated that significantly more bone was formed ($p<0.0001$) with higher apparent density ($p<0.01$) in the bone defects transfected with a BMP-6 plasmid. All defects treated with BMP-6 healed completely, while none of the BMP-2 treated defects or controls healed.

Example 4

Biochemical Studies of BMP Addition

Figure 5:
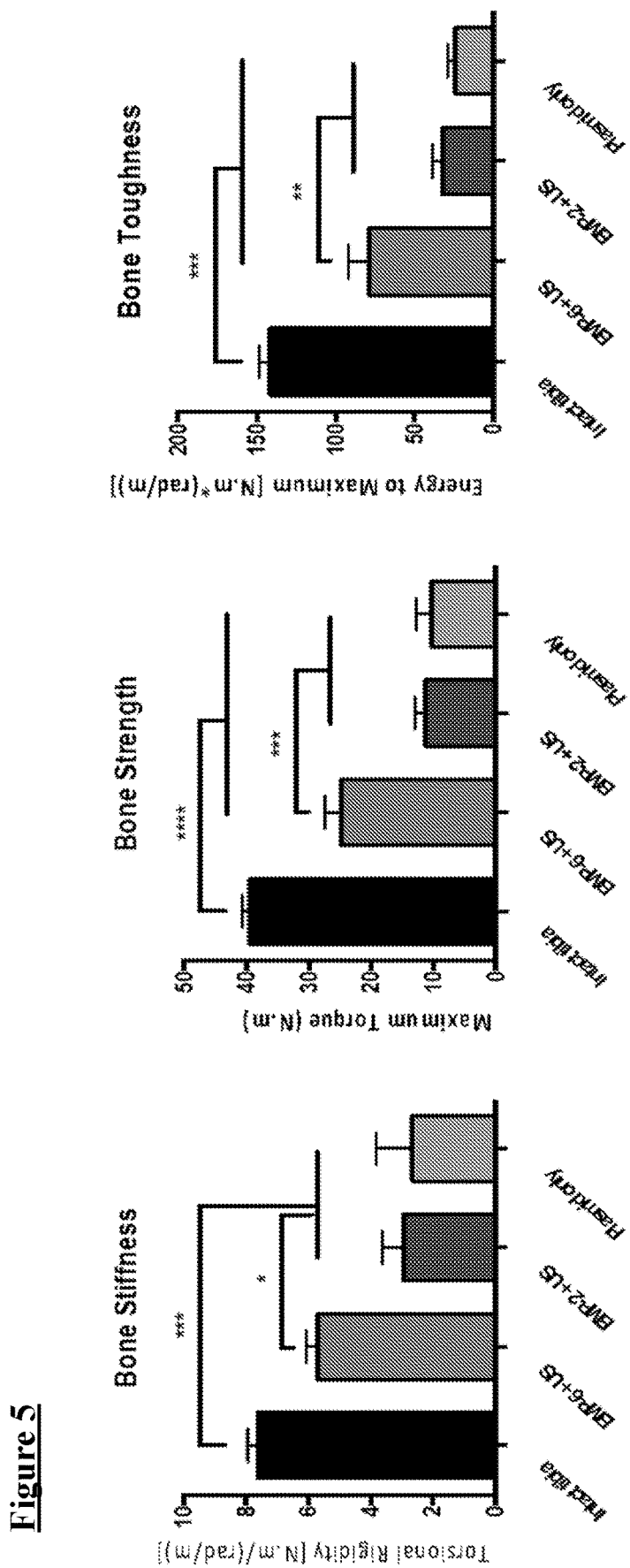

In accordance with the microCT analysis results, further biomechanical analysis of the treated bones revealed mechanical superiority of defects treated with BMP-6. Tibial defects treated with BMP-6 and ultrasound and intact tibiae were significantly stiffer, stronger and tougher than tibiae treated with BMP-2 and ultrasound or a plasmid only control ($p<0.05$) (FIG. 5). No significant differences in stiffness were found between intact tibiae and BMP-6 and ultrasound treated tibiae ($p>0.05$) further demonstrating the superior biomechanical properties of BMP-6 and ultrasound treated tibiae.

Example 5

Focus on Osseointegration at Bone Tendon Interface

Of interest is understanding whether these results can be applied to develop a similar approach for acceleration of allograft-bone integration in an ACL reconstruction model. The Inventors believe that BMP proteins can be used to enhance osseointegration of tendon allografts. Delivery of such factors via recombinant proteins and viral vectors have their associated caveats when compared to non-viral gene delivery. Despite these promising approaches, it has not been demonstrated that non-viral methods could induce similar results in reference to models of ACL reconstruction.

Figure 6:
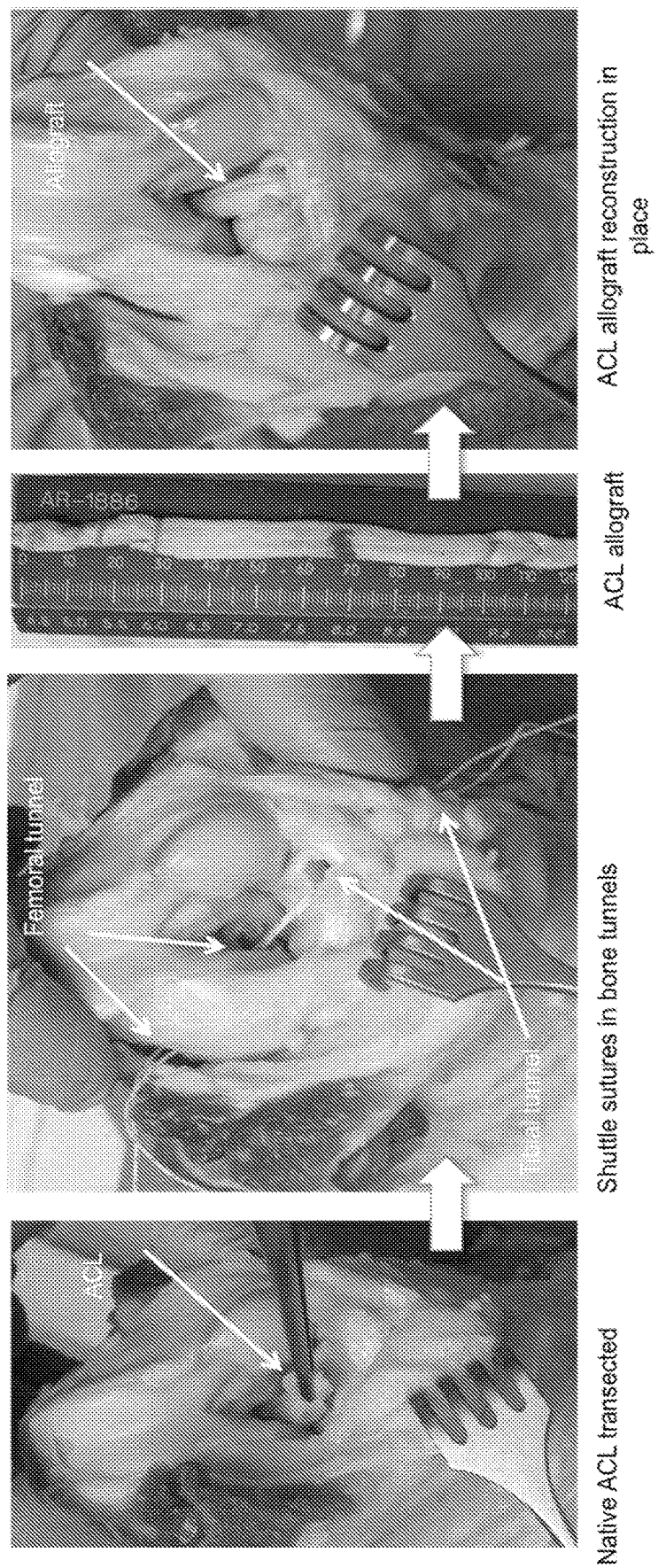
Figure 9:
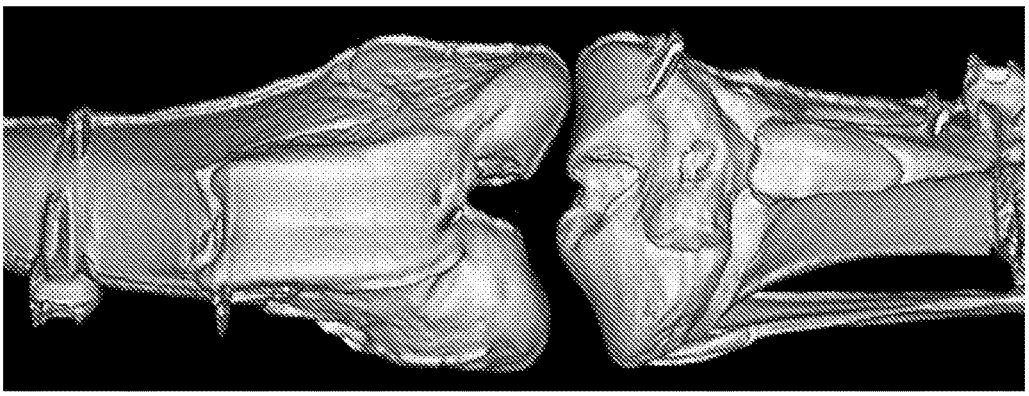
Figure 9:
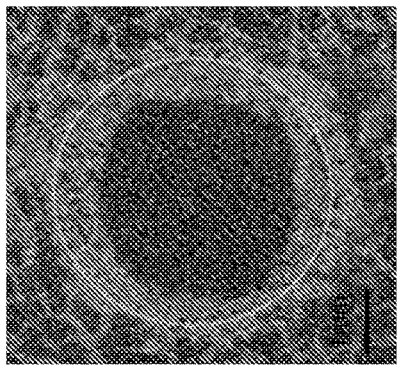
Figure 9:
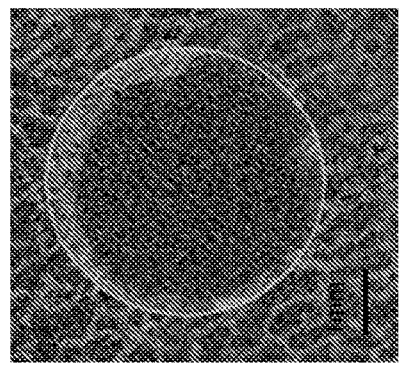
Figure 9:
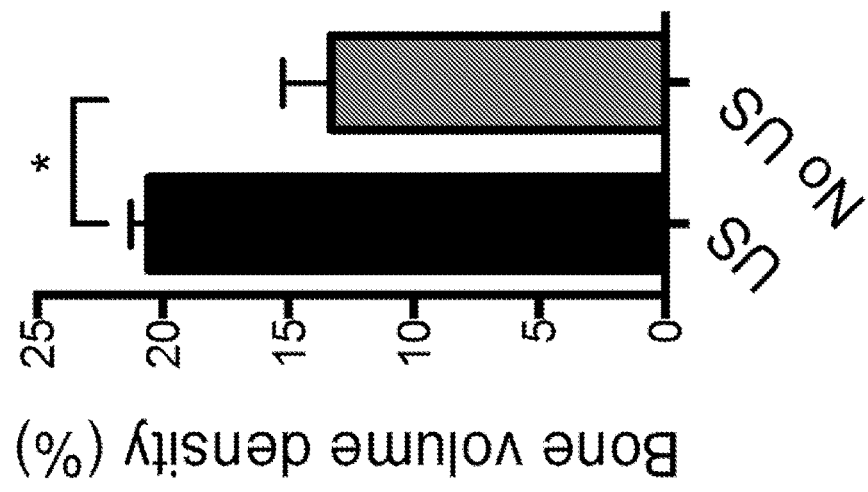

Here, the Inventors first harvested pig flexor tendons from non-survival surgeries. Pig tendons were sent to Veterinary Transplant Services Inc. for bacteriological tests and preparation of sterile allografts. Next ACL reconstruction was performed using a mini-pig model. After transection of the ACL in a mini-pig, the previously prepared allografts were implanted into femoral and tibial tunnels with cortical screw fixation (FIG. 6). Importantly, a collagen scaffold (DuraGen, Integra LifeSciences) was also implanted at the two ends of the allograft tissue within the tibial and femoral bone tunnels.

Fourteen days post operation the Inventors injected a GFP plasmid suspended in MBs, under fluoroscopic guidance, into both the femoral and tibial tunnels (FIG. 7A). Next, transcutaneous ultrasound was applied only to the femoral tunnel (FIG. 7B). Five days later, the, mini-pigs were sacrificed and the cells from within the bone tunnels were analyzed using flow cytometry. The Inventors' results showed that about 50% of the cells in the femoral tunnel expressed GFP (FIG. 7C). The Inventors also noted that 12-22% of the cells in the bone tunnels expressed MSC markers (FIG. 7D).

Example 6

Focus on Osseointegration at Bone Tendon Interface

Without being bound by any particular theory, the Inventors propose use of targeted BMP gene delivery to resident stem cells to enhance tendon allograft integration into bone in a large animal model (FIG. 8).

After transection of the native ACL, one can reconstruct the ACL in mini-pigs using a flexor tendon allograft, which is then inserted into bone tunnels at the tibia and femur, as shown in FIG. 6. The tibial and femoral portions of the graft are wrapped with a collagen scaffold in order to recruit host progenitors to the bone tunnel sites. Two weeks post-surgery a BMP gene, suspended in MBs, are injected into the ACL reconstruction bone tunnels under fluoroscopic guidance (FIG. 7A). This is followed by an ultrasonic pulse application to the tunnels in order to facilitate intracellular delivery of the therapeutic gene into host local MSCs populating the implanted scaffold. This leads to enhanced ACL graft integration into the host bone (FIG. 7B).

The use of ultrasound-mediated gene delivery to endogenous stem cells to enhance tendon allograft-bone healing can provide a significant number of benefits to a wide variety of patients suffering from soft-tissue structure injuries in the musculoskeletal system.

Example 7

Study Design

The objective of the Inventors' study was to develop a novel therapy consisting of ultrasound-mediated gene targeting to endogenous MSCs for critical-sized bone fracture repair. The Inventors' pre-specified hypothesis was that ultrasound-mediated, microbubble-enhanced gene delivery of a BMP-6 gene would lead to efficient bone regeneration and fracture healing in a clinically-relevant, large animal model. Male and female Yucatan mini-pigs (S&S Farms) were used in this study. The mean weight±SD of the animals was 37.0±3.6 kg and their mean age±SD was 7.8±1.2 months. The sample size used was estimated to achieve a power of 0.8 and α=0.05 using one-way ANOVA.

Sonoporation was investigated for its capacity to regenerate a critical-sized tibial bone fracture. Pigs underwent surgery and a 1 cm critical-sized bone fracture was created in their tibia bone. Collagen scaffold was implanted within the fracture site to recruit endogenous MSCs. Fourteen days later, the pigs were randomly assigned to receive either the treatment, which consisted of BMP-6 plasmid premixed with microbubbles injection to the fracture site followed by ultrasound application ("BMP-6+US" group), or to one of the control groups. The following control groups were used: 1) No treatment ("Scaffold only" group); 2) BMP-6 plasmid premixed with microbubbles injection ("BMP-6" group); or 3) Empty plasmid vector premixed with microbubbles injection followed by ultrasound application ("US only" group). Additionally, a control group treated with an autograft ("Autograft" group) was used to assess the Inventors' treatment efficacy compared to the gold-standard treatment for large fractures. Sonoporation potency was estimated using reporter gene expression and tissue analysis for BMP-6 gene and protein expression. Bone formation was assessed using micro-computed tomography, histology and biomechanical testing. Animals that developed acute procedural complications such as bone fixation failure or signs of distress during follow-up that compromised animal welfare were eliminated from the study.

Example 8

Plasmid DNA Production

Plasmids encoding for luciferase2 under the control of the ubiquitin promoter (pUb-Luc2) and enhanced green fluorescent protein under the control of the cytomegalovirus promoter (pCMV-EGFP-N1) were used to study transgene expression. A plasmid encoding for BMP6 under the control of the cytomegalovirus promoter (pCMV-BMP6) was used to induce bone regeneration. Plasmid preparation was detailed elsewhere. All plasmids were expanded using standard laboratory procedures and purified using an EndoFree Kit (Qiagen, Valencia, Calif.).

Example 9

Critical-Sized Tibia Fracture Model: Surgical Procedure

Figure 16:
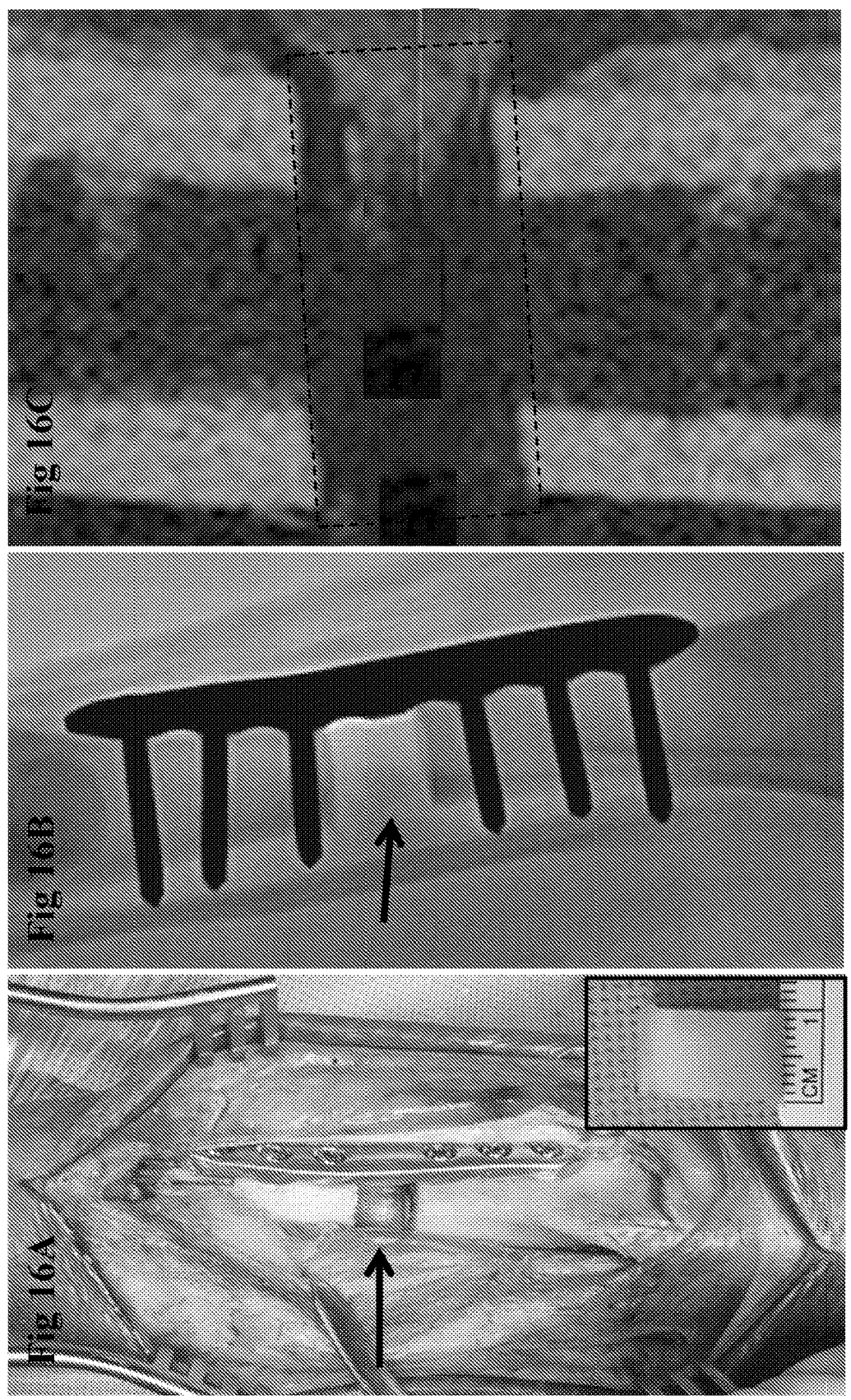

All animal procedures were approved by the Cedars-Sinai Medical Center institutional review board for animal experiments. A critical-sized circumferential bone defect of 1 cm in length was created in the tibia bones of Yucatan mini-pigs per previously described method. A critical-sized defect in humans was defined as involving 50% of the cortical diameter of the tibia and >1 cm in length". The average length of the tibia bone in the Yucatan minipig is 10 cm, and in an adult human it is 43 cm. Hence, a 1-cm defect in the minipig can be compared to a 4.3 cm defect in an average person. Following an 18-hour preoperative fast, each mini-pig was sedated using intramuscular acepromazine (0.25 mg/kg), ketamine (20 mg/kg), and atropine (0.02-0.05 mg/kg). The animal was then administered propofol (2 mg/kg) intravenously and endotracheal intubation was performed. Anesthesia was maintained using 1-3.5% inhaled isoflurane for the duration of the procedure. A 10-cm anteromedial skin incision was made over the tibia. Soft tissue and periosteum were bluntly dissected to expose the tibial diaphysis. An oscillating saw (ConMed, Largo, Fla.) was used to remove 1 cm of bone and create a segmental bone fracture. The fracture was internally fixated using a custom made 6-hole limited-contact dynamic compression plate (Veterinary Orthopedic Implants, St. Augustine, Fla.; FIG. 16), and a flat sheet of biodegradable collagen scaffold (DuraGen Matrix, Integra LifeSciences) with pore size of 100 µm was shaped and implanted in the fracture site. For autograft-treated animals, the resected bone segment was grafted into the fracture and fixated using the fixation plate. Finally, the subcutaneous tissue was closed with an absorbable subcutaneous suture and the skin was closed using a nonabsorbable suture, which was removed two weeks after surgery. The animal received perioperative antimicrobial prophylaxis (ceftiofur 0.05 ml/kg) and postoperative analgesia (buprenorphine 0.2 mg/kg).

Example 10

Flow Cytometry Characterization of Cells Recruited to Fracture Site

Nine animals underwent surgery and were anesthetized and sacrificed by injection of veterinary euthanasia solution (Vetone, Boise, Id.) on postoperative days 7, 14 and 21. Post-mortem, tissue was extracted from the fracture site, washed with PBS, digested using 0.1% collagenase (type 1A, Sigma-Aldrich, St. Louis, Mo.) for one hour, filtrated using a 70 µm cell strainer and centrifuged at 2000 rpm for seven minutes. Freshly isolated cells were analyzed for MSC surface markers, taking into consideration the limited availability of anti-pig antibodies. The cells were stained with mouse anti-human (with cross-reactivity to pig) CD90 and mouse anti-pig CD29 (BD Biosciences Pharmingen, San Diego, Calif.). Both primary antibodies were detected by applying fluorochrome-conjugated secondary antibodies rat anti-mouse-PE (BD Biosciences Pharmingen) according to the manufacturer's recommendations. The cells were analyzed and plotted using an LSR-II flow cytometer, BD FACSDiva, and FCS Express software (BD, Heidelberg, Germany). Nonspecific binding of secondary antibodies was quantified, and the fluorescence signal was subtracted from the detection values of the experimental group.

Example 11

Ultrasound-Mediated Microbubble-Enhanced Gene Delivery

Fourteen days post fracture creation, scaffold implantation and bone stabilization, each animal was sedated in the manner described above. First, a microbubble suspension (Definity, Lantheus Medical Imaging, N. Billerica, Mass.) was activated by 45 seconds of shaking using a Vialmix shaker (Lantheus Medical, N. Billerica, Mass.). Then $10^7$ microbubbles and 1 mg plasmid DNA were mixed together. To avoid microbubble aggregation and adhesion to syringe walls, the syringe containing the mixture was manually rotated periodically prior to injection. Next, the fracture was located using a fluoroscan mini C-arm (Hologic, Bedford, Mass.) and an 18 G needle was inserted into the center of the fracture (FIG. 18A). The mixture was injected while being visualized using a Sonos 5500 (Philips Ultrasound, Andover, Mass.) unit equipped with a focused S3 probe set to B-mode with its focal point matching the location of the defect (FIG. 18B, C). Then, a therapeutic ultrasonic pulse was applied using cadence contrast agent imaging mode at a transmission frequency of 1.3 MHz, mechanical index of 0.6, and a depth of 4 cm for approximately 2 minutes until all visualized microbubbles burst (FIG. 18D).

Example 12

Transfection Efficacy Evaluation—GFP Expression

Six animals underwent surgery. Fourteen days later, the mini-pigs were injected with GFP plasmid premixed with microbubbles. The animals were randomly assigned so only half were treated with ultrasound immediately after the injection. Five days post-transfection the animals were sacrificed. Ex vivo optical imaging of the fracture site was performed using a fluorescence imaging system (IVIS; Perkin Elmer, Waltham, Mass.) to localize the signal within the treated limb. Then, cells from the fracture sites were isolated as described above. The cells were examined using flow cytometry to detect GFP expression. The percentage of GFP-positive cells served as a measure of transfection rate.

Example 13

Transfection Efficacy Evaluation—Luciferase Expression

Six animals underwent surgery and 14 days later were injected with Luciferase plasmid premixed with microbubbles. The animals were randomly assigned so only half were treated with ultrasound immediately after the injection. Five days post-transfection, cells from the fracture sites were isolated as described above and incubated with luciferase lysis buffer (Promega, Madison, Wis.). The resulting homogenate was centrifuged at 10,000 g for 10 min, and 100 µl of luciferase reaction buffer (Promega) was added to 20 µl of the clear supernatant. Light emission was measured by a luminometer (TD-20/20; Turner BioSystems, Sunnyvale, Calif.) in RLU. The values were normalized for protein content, which was measured using bicinchoninic acid assay (Pierce, Rockford, Ill.). Luciferase activity was expressed as RLU/mg of protein.

Example 14

BMP-6 Gene and Protein Expression Analysis

Eighteen animals underwent surgery and 14 days postoperatively were injected with BMP-6 plasmid premixed with microbubbles. The animals were randomly assigned so only half were treated with ultrasound immediately after the injection. Then, animals were randomly sacrificed 2, 5 or 10 days after ultrasound transfection. Tissues were collected post-mortem to characterize BMP-6 gene and protein expression.

Quantitative RT-PCRs were done to estimate BMP-6 gene expression in various organs following ultrasound transfection. Tissues from the fracture site, brain, bone marrow, lung, liver, heart, skeletal muscle and spleen were harvested post-mortem and RNA was isolated using RNeasy extraction kit (Qiagen, Valencia, Calif.). The RNA was then reverse transcribed using random primers and reverse transcriptase (Promega). Expression of BMP-6 gene was analyzed using the ABI7500 Prism system (Applied Biosystems, Foster City, Calif.). 18s was used as a housekeeping gene control.

ELISA was used to estimate BMP-6 protein expression in fracture over time. Tissue from the fracture site was homogenized using tissue homogenizer (VWR, Radnor, Pa.) and incubated with proteinase inhibitors (Roche, Basel, Switzerland) at 4° C. for two hours. The resulting homogenate was centrifuged at 12,000 rpm for 10 minutes, and the supernatant was collected for a BMP-6 ELISA assay (R&D Systems, Minneapolis, Minn.). Values were normalized for protein content, which was measured using bicinchoninic acid assay (Pierce).

Example 15

Bone Formation Analysis Using Micro-Computed Tomography

Twenty-eight mini-pigs underwent surgery and were randomly assigned to receive the following 14 days later: 1) No treatment ("Scaffold only" group); 2) BMP-6 plasmid premixed with microbubbles ("BMP-6" group); 3) Empty plasmid vector premixed with microbubbles and ultrasound ("US only" group); 4) BMP-6 plasmid premixed with microbubbles and ultrasound ("BMP-6+US" group); or 5) Autograft implantation. Eight weeks postoperatively, the animals were euthanized, and their tibiae were harvested for ex vivo, high-resolution micro-computed tomography (vivaCT 40; Scanco Medical AG, Brüttisellen, Switzerland), as previously described. Microtomographic slices were acquired using an X-ray tube with a 55 kVp potential and reconstructed at a voxel size of 35 µm. The fracture was evaluated using histomorphometric 3D evaluation. A constrained 3D Gaussian filter ($\sigma=0.8$, support=1) was used to partly suppress noise in the volume of interest. The bone tissue was segmented from marrow and soft tissue using a global thresholding procedure. A quantitative assessment of bone volume density and apparent density based on microtomographic data sets was created using direct 3D morphometry.

Example 16

Histological Evaluation

One specimen from each treatment group was used for histological evaluation. The specimens were cleaned and fixed in 4% formalin for 3 days. Dehydration was accomplished using a graded series of ethyl alcohols and three stages of Xylene. Infiltration was performed using a graded series of xylene and Osteo-Bed (Polysciences, Warrington, Pa.) resins, followed by a catalyzed mixture of Osteo-Bed resin containing 1.40 g of benzoyl peroxide per 100 ml. Embedding was performed using a final catalyzed resin mixture of Osteo-Bed resin solution containing 2.5 g of benzoyl peroxide per 100 ml. Tissue sections were cut at a section thickness of 5.0 µm on a Leica RM2155 rotary microtome (Leica, Wetzlar, Germany) by using tungsten carbide D-profile knives. The sections were stained using matrix-specific Masson's trichrome staining. In brief, tissue sections were treated overnight in Bouin's solution at room temperature. Slides were rinsed for 10 min under running water and stained with Weigert's hematoxylin for 5 min. The slides were then rinsed and stained with scarlet-acid fuchsin for 5 min and rinsed again, after which the slides were again stained with phosphomolybdic-phosphotungstic, aniline blue, and 2% acetic acid for 5 min each. Finally, the slides were rinsed, dried, and mounted. The slides were imaged using a four-channel Laser Scanning Microscope 780 (Zeiss, Pleasanton, Calif.) with ×20 magnification, z-stacking, and 5×5 tile scanning. For zoom-in images, a single z-stacked image was generated. All samples were scanned using the same gain and exposure settings.

Example 17

Biomechanical Analysis

Fifteen samples from the "Autograft", "BMP-6+US" and "BMP-6 only" groups (n=5 per group) were used for biomechanical analysis. Following harvest, the samples were wrapped in saline-soaked gauze, sealed and frozen until analysis. Prior to analysis, the samples were thawed for approximately 1 hr and then allowed to rehydrate in PBS for 2 hrs. A custom-made alignment jig was used to fix the proximal and distal ends of the tibia in two aluminum square pots by submerging 1" of each end in Bosworth Fastray Cement (Midway Dental Supply, Lakeville, Ind.). The gage length of the exposed tibia between the two fixed ends was measured using calipers prior to testing. Torsion testing was performed using a custom designed jig on an Instron ElectroPuls 10000 (Instron, Norwood, Mass.). The rotational actuator was rotated at a rate of 1 deg/sec until failure. Load and rotation data were continuously recorded during testing. The collected data was analyzed using a custom MATLAB code to determine the torsional rigidity, yield torque, ultimate torque, rotation to yield torque, rotation to ultimate torque, work to yield torque, and work to ultimate torque.

Example 18

Statistical Analysis

GraphPad Prism 5.0f software (GraphPad Prism, San Diego, Calif.) was used to analyze the data. Results are presented as means±SE. Data analysis was conducted using a one-way ANOVA or a two-way ANOVA with Tukey's multiple comparison post hoc test. To assess significance, $p<0.05$ was considered statistically significant.

Example 19

Figure 11:
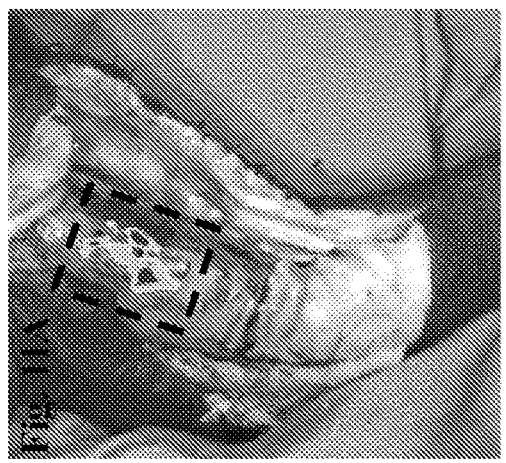
Figure 11:
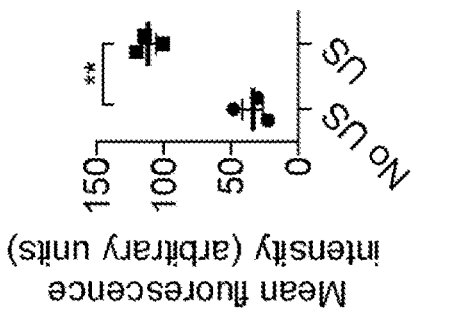
Figure 11:
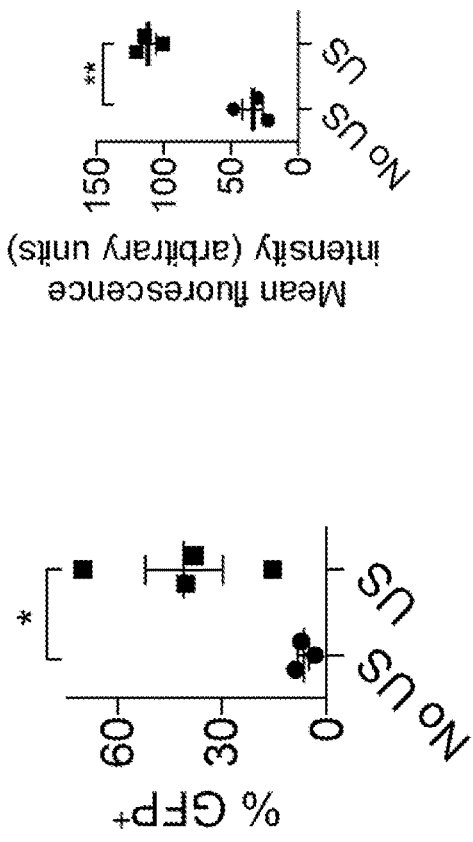
Figure 11:
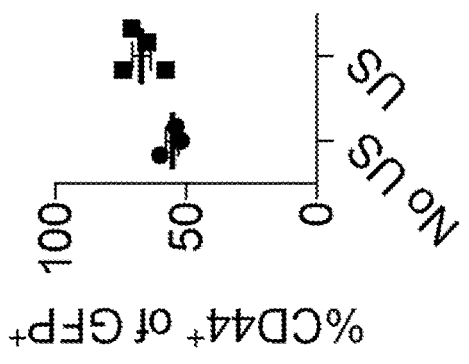
Figure 11:
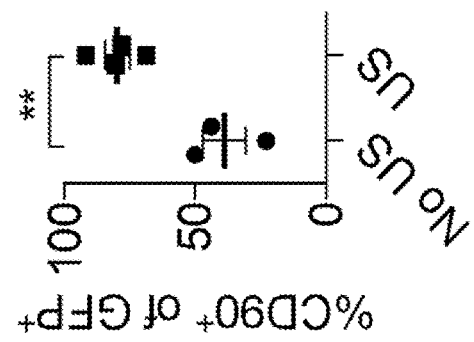
Figure 11:
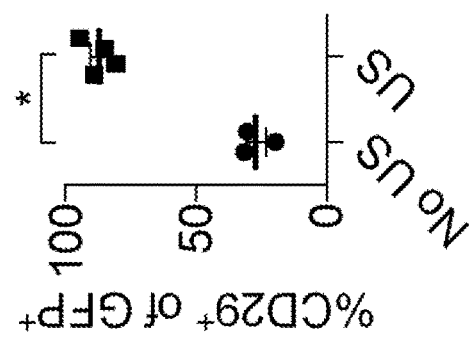
Figure 11:
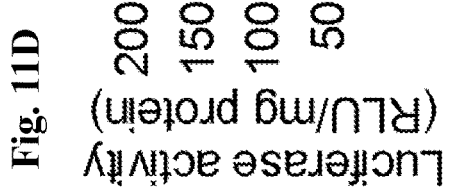
Figure 18:
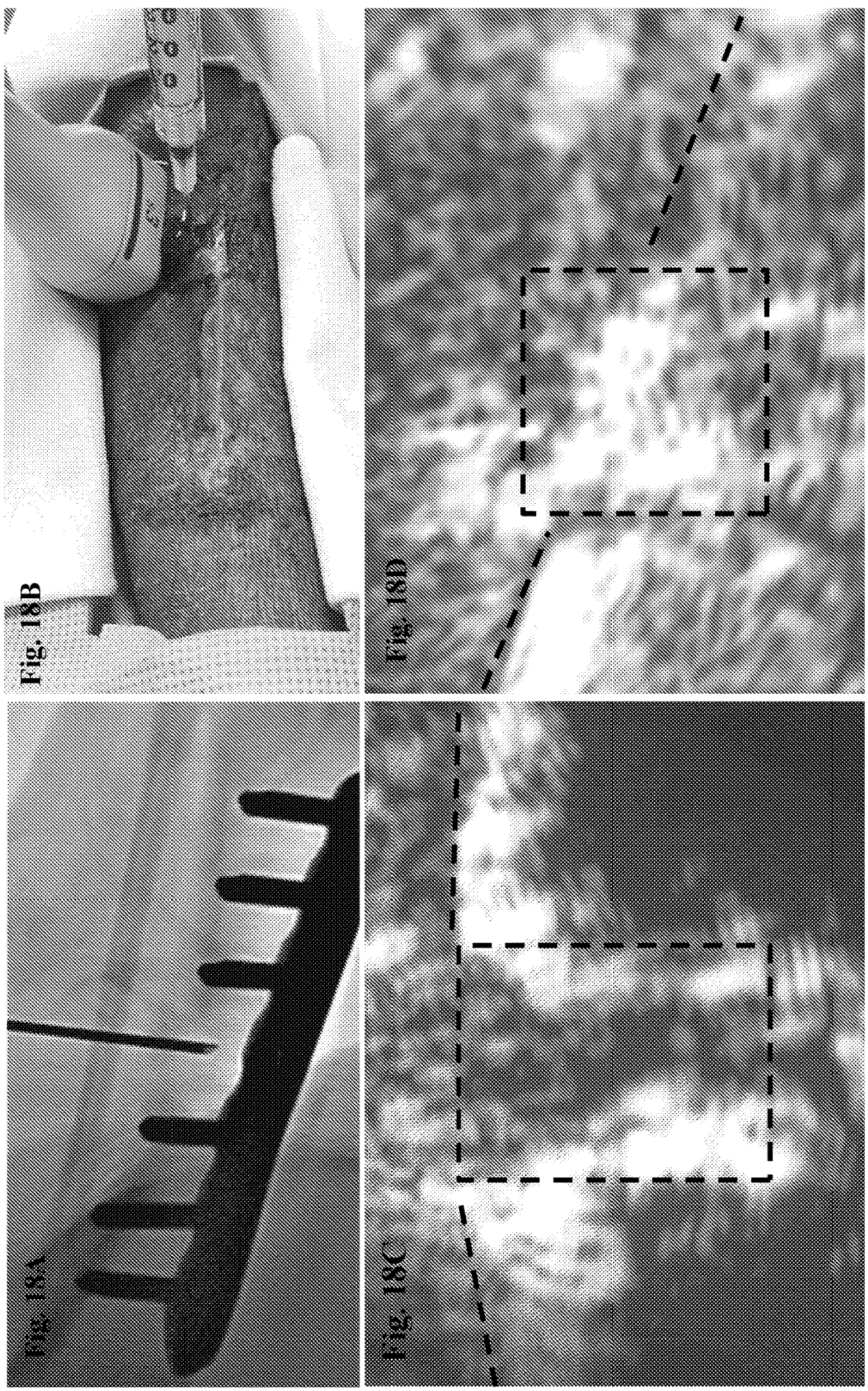

Sonoporation Leads to Reporter Gene Expression in Endogenous MSCs Recruited to Fracture Site Mini-pigs underwent surgery during which a 1-cm critical-sized tibial bone fracture was created and a biodegradable collagen scaffold was implanted (FIG. 16). The fracture sites were treated with microbubble-enhanced ultrasound-mediated gene delivery 14 days after surgery, when maximal cell recruitment of mesenchymal lineage was noted (FIG. 17). Plasmid DNA encoding to a reporter gene, either green fluorescent protein (GFP) or luciferase, mixed in microbubbles was transcutaneously injected into the fracture site, and half of the animals were randomly treated with ultrasound (FIG. 18). Ex vivo optical imaging of the fracture site revealed a well-localized fluorescent signal at the fracture site for GFP-treated animals (FIG. 11A). Flow cytometry revealed that 40% of cells collected from within the tibial fracture of animals treated with ultrasound ("US" group) expressed GFP, six times greater than that observed in untreated animals ("No US" group, $p<0.05$; FIG. 11B). GFP-expressing cells from bone fractures in ultrasound-treated animals were also three times more fluorescent ($p<0.01$, FIG. 11C) and demonstrated 80 times more luciferase activity than cells from fracture sites in animals not subjected to ultrasound ($p<0.05$, FIG. 11D). Interestingly, an examination of the transfected cells showed significantly more cells expressing the MSC markers CD29 and CD90 in the ultrasound treated group. Ninety percent of GFP-positive cells in the ultrasound-treated group were CD29-positive and 80% of GFP-positive cells were CD90-positive, whereas only 30% of GFP-positive cells in the untreated group were CD29 positive and 40% were CD90 positive ($p<0.01$; FIG. 11E, F). No significant differences were observed in CD44-positive cells ($p=0.07$; FIG. 11G). Overall, ultrasound-treated fracture sites exhibited significantly higher progenitor transfection rates as well as stronger transgene expression levels.

Example 20

Sonoporation Induces Transient BMP-6 Expression at Bone Fracture Site

Eighteen pigs were operated as described above and treated with either ultrasound-mediated BMP-6 and microbubbles gene delivery ("BMP-6+US" group) or injection of BMP-6 and microbubbles without ultrasound application (control "BMP-6" group). Local expression of BMP-6 gene following sonoporation to tibial bone fractures was evaluated over time.

The mixture (DNA and microbubbles) was injected while being visualized using a Sonos 5500 (Philips Ultrasound, Andover, Mass.) unit equipped with a focused S3 probe set to B-mode with its focal point matching the location of the defect (FIG. 18B, C). Then, a therapeutic ultrasonic pulse was applied using cadence contrast agent imaging mode at a transmission frequency of 1.3 MHz, mechanical index of 0.6, and a depth of 4 cm for approximately 2 minutes until all visualized microbubbles burst (FIG. 18D). For ACL studies, the same parameters were applied with a mechanical index of 1.2 and depth of 3 cm.

Figure 19:
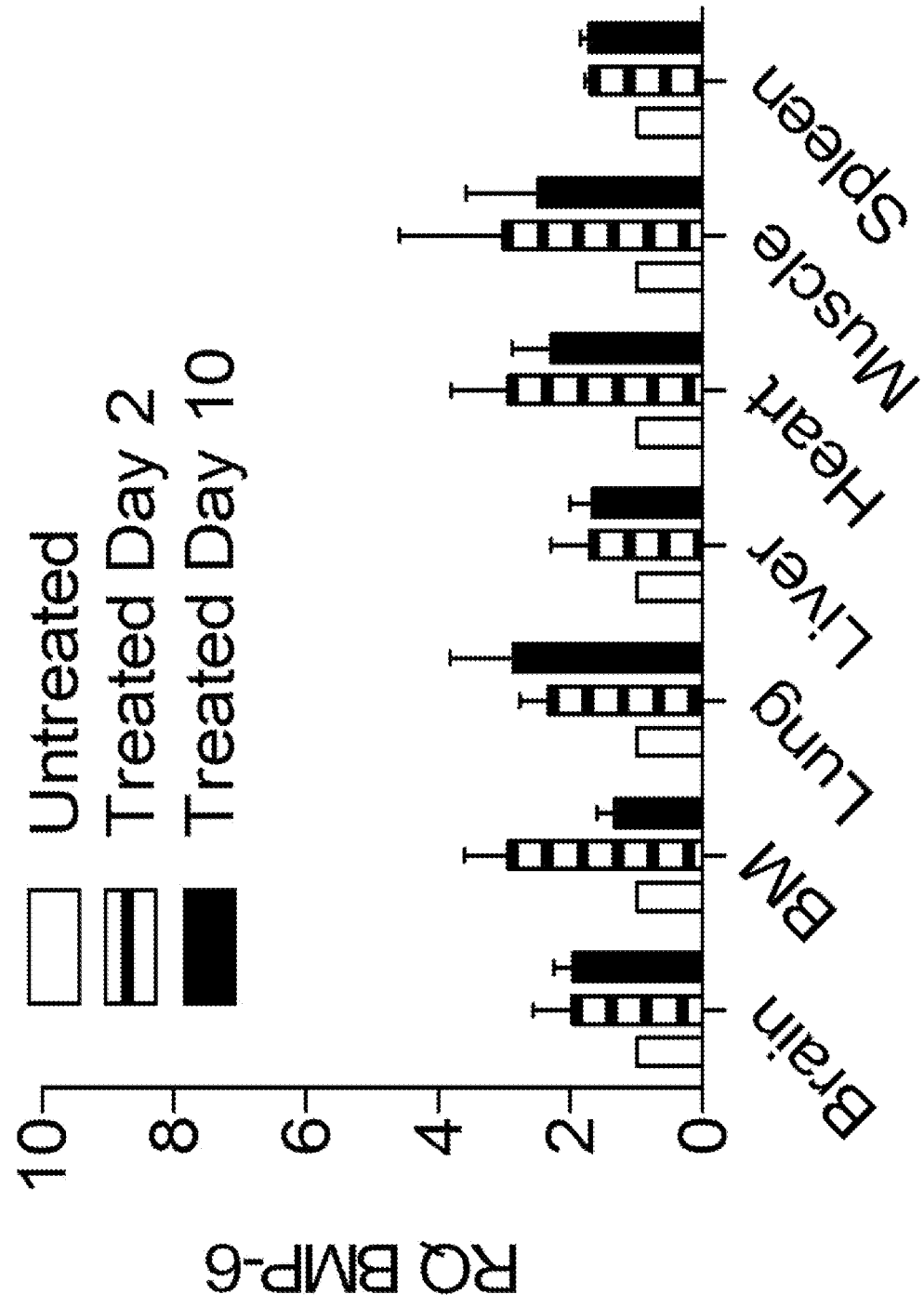

Quantitative PCR analysis of isolated cells from the fracture site showed 850- and 400-fold higher BMP-6 expression in ultrasound-treated animals compared to control animals on days 2 and 5 post treatment, respectively ($p<0.05$, FIG. 12A). On day 10, BMP-6 gene expression levels were undetectable. Similarly, BMP-6 protein secretion levels in the fracture site were 70- and 120-fold higher compared to animals that were not treated with ultrasound, on days 2 and 5 post treatment, respectively ($p<0.01$, FIG. 12B). Negligible levels of BMP-6 protein were detected on day 10. In addition, no over-expression of BMP-6 was found in off-target tissues (FIG. 19).

Example 21

BMP Sonoporation Facilitates In Vivo Bone Regeneration

Figures 13, 13C:
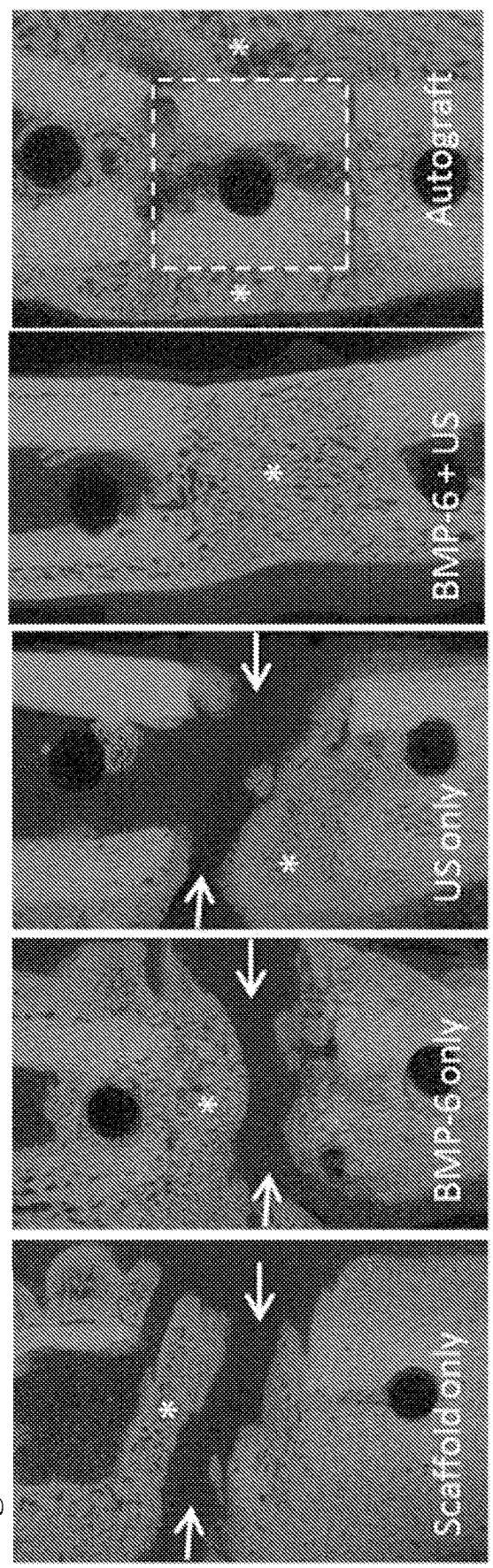
Figures 13, 13D:
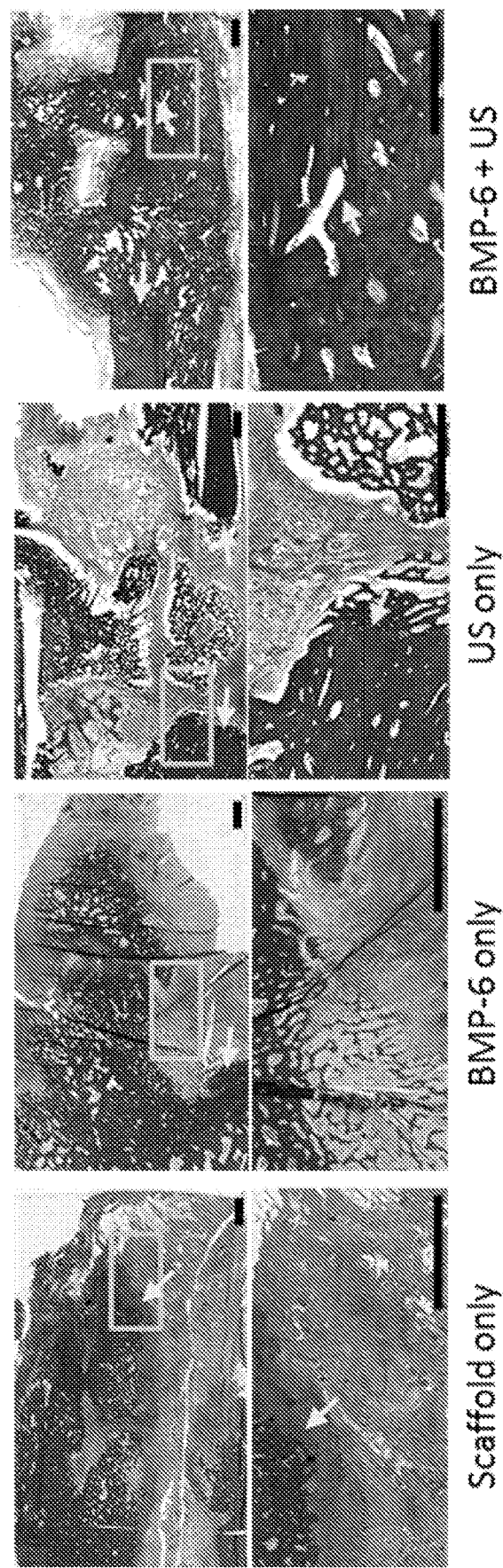

Next, the therapeutic effect of local BMP-6 gene delivery was evaluated in the same pig model of tibial non healing fracture. Twenty-eight animals were operated as described above. Tibial fracture regeneration in BMP-6 and ultrasound ("BMP-6+US" group) treated animals was compared to a non-treated control group ("Scaffold only" group), animals treated with either only plasmid premixed with microbubbles injection without ultrasound ("BMP-6 only" group) or an empty plasmid premixed with microbubbles and ultrasound ("US only" group), and a gold standard control group treated with an autograft ("Autograft" group). Micro-computed tomography (μCT) analysis eight weeks after surgery revealed that fractures treated with BMP-6 and ultrasound regenerated 75% of its volume with new-formed bone, which was equivalent to autograft transplantation (p>0.05) and doubled all other treatment groups (p<0.001; FIG. 13A). No differences in healing were noted between male and female pigs treated with BMP-6 and ultrasound (p=0.119, n=4 per group). Additionally, the new-formed bone in the "BMP-6+US" group was significantly more calcified than all other groups (p<0.01; FIG. 13B) except the "Autograft" group (p>0.05). Importantly, only fractures treated with BMP-6 and ultrasound ("BMP-6+US") or autograft showed union, evident by the complete cortical continuity of the tibia (FIG. 13C). Histological analysis showed that there was a complete regeneration of the fracture with mature new-formed bone and the presence of osteocytes in BMP-6 and ultrasound treated pigs (FIG. 13D). In all other groups, however, insufficient bone formation was found along abundant granulation tissue deposition and fibrosis (FIG. 13D).

Example 22

BMP-6 Gene Delivery Induces Functional Healing of Treated Bones

Torsional testing was performed blindly on tibiae excised from the operated animals to examine the mechanical properties of the treated bones 8 weeks after surgery. In accordance with the μCT and histological analysis results, tibial bones from the "BMP-6+US" group showed at least twofold higher mechanical stiffness, strength and toughness compared with tibial fractures from the "BMP-6 only" group (p<0.05, FIG. 14). No significant differences were observed between the "BMP-6+US" and the autograft groups (p>0.05).

Example 23

Discussion

Figure 15:
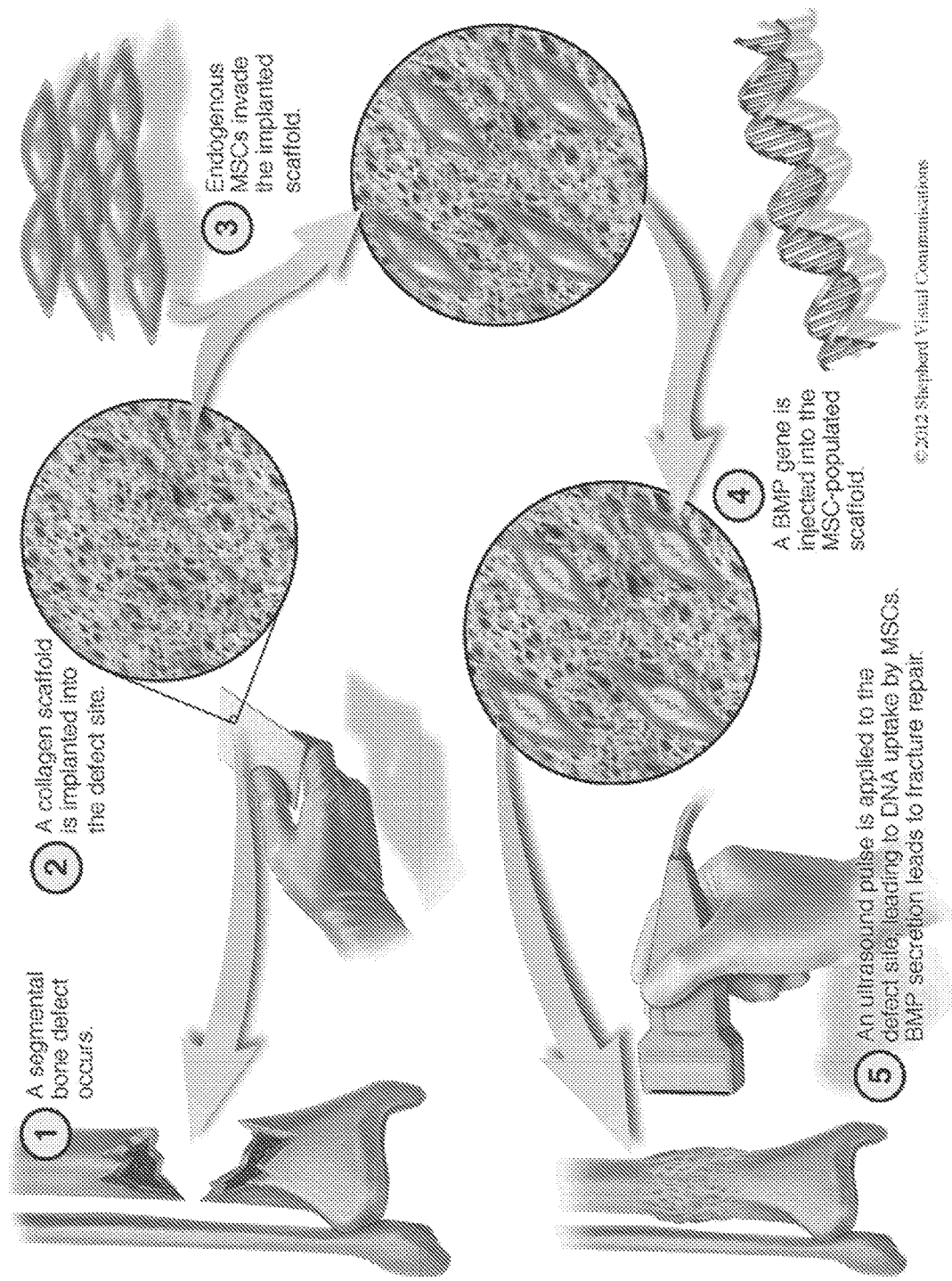

In this study, the Inventors present the use of ultrasound-mediated, microbubble-enhanced gene delivery for in situ bone engineering in a large animal model (FIG. 15). The Inventors were able to show that ultrasound-mediated gene delivery to cells residing within the fracture site achieved transient local gene expression, mainly targeting endogenous MSCs. Osteogenic gene delivery resulted in a spatial and temporal expression pattern that is consistent with non-viral gene delivery systems. Furthermore, it resulted in complete fracture union eight weeks postoperatively, and autograft-equivalent biomechanical properties. In this study, the Inventors used a clinical ultrasound system within its intended range of parameters, which includes the use of contrast imaging. Based on the consensus in the field, the Inventors were using an ultrasonic energy within the safe range. Indeed, no signs of heating or heat-associated damage were evident clinically and histologically following ultrasound exposure. Importantly, no evidence of ectopic transgene expression or inflammatory response was observed, suggesting a favorable safety profile. To the best of the Inventors' knowledge this is the first report showing successful sonoporation-induced gene delivery and bone regeneration in a clinically relevant, large animal model.

It has been reported that nonviral gene delivery can achieve complete fracture repair in a large animal model (canine). Using gene-activated matrix implants containing plasmid DNA encoding human parathyroid hormone, complete critical-sized tibial fracture repair was achieved by 18 and 8 weeks for 1.6 cm and 1.0 cm sized fractures, respectively. Since then, other works involving large animals focused mainly on viral gene delivery. This includes reports showing improved fracture repair following BMP-2 adenoviral gene delivery in a tibial fracture in osteoporotic sheep. Other reports demonstrate improved fracture repair following implantation of BMP-2 virally transduced bone marrow derived mesenchymal stem cells into a goat tibial fracture. Despite these promising results, viruses have many safety concerns, limiting their use in humans. Other reports have observed that adenoviral BMP-2 gene delivery to a fracture site resulted in temporary cellular and persistent humoral immune responses against the viral vector. In addition, clinical trials have shown that viral gene delivery can evoke a systemic inflammatory response resulting in death, and may cause carcinogenesis by random gene insertions into the genome. Thus, efficient nonviral gene delivery methods must be developed for clinical use.

Until this study, ultrasound-mediated BMP gene delivery has not been successfully applied for fracture repair. Researchers have used microbubble-enhanced ultrasound-mediated gene delivery of BMP-2 and BMP-7 in a femur nonunion model in rats. In spite of successfully inducing gene overexpression and ectopic bone formation using repetitive treatments, they could not induce significant orthotopic bone formation in a fracture site. These differences can be attributed to diminished osteogenic potential of BMP-2 and BMP-7 within the fracture site microenvironment, as reported in other animal and clinical studies. The biological response to BMPs is dependent on the cell type and microenvironment that is present at the site of BMP delivery. BMP-6 has a distinct BMPR-IA receptor specificity, making it less affected by endogenous BMP inhibitors, while strongly promoting osteogenesis by osteoblasts. In the Inventors' previously published report, the Inventors showed that BMP-6 has better osteogenic potential and induced more efficient bone formation than BMP-2, both in vitro and in vivo, when overexpressed in MSCs. Some studies have suggested that BMP-6 signaling works through mechanisms of both osteochondral and intramembranous ossifications, with the latter being the primary pathway, thus resulting in more rapid calcification within the fracture site. Therefore, BMP-6 could serve as a more potent orthotopic bone inducer.

Another difference between the Inventors' study and the study conducted by Feichtinger et al. is the two-step procedure, which includes recruitment of endogenous progenitor cells to the fracture site. This study showed that by implanting a collagen scaffold into the fracture site, efficient endogenous progenitor migration and retention in the scaffold can be achieved within 14 days after the surgery.

Interestingly, it has been reported that a delayed administration of a BMP-2 encoding adenoviral vector improved bone formation in a critical-sized femoral fracture in rats. It is likely that a delayed treatment allows for more progenitors to populate the fracture site, making the vector more efficient in targeting cells that respond to BMP secretion and induce bone regeneration. Overall, it seems that the combination of a potent osteogenic protein together with an effective delivery strategy to a viable progenitor population is key to efficient fracture repair.

A modification of the method described here could include pre-loading of microbubbles and plasmid into the scaffold, which would eliminate the need to inject these materials later. A recent paper used fibrin/collagen hybrid-matrices containing microbubbles, BMP2/7 co-expression plasmids together with C2C12 cells to which ultrasound was applied immediately following intramuscular implantation in mice. Although that study combined exogenous cells within the scaffold, only little amount of new bone was generated in vivo. In the Inventors' proposed method, the recruitment of endogenous progenitor cells is an important factor as the Inventors have previously shown in rodents and that process could take at least two weeks. Hence, implanting scaffolds containing plasmids and microbubbles would require long-term protection of these components since naked DNA is degraded by DNAases and microbubbles have a short half-life of approximately 10 minutes when injected locally. To the best of the Inventors' knowledge, there are technological barriers that still need to be overcome in order to generate such a composite scaffold.

The clinical gold standard for nonunion treatment utilizes autografts. As a living tissue, their osteoinductive and osteoconductive properties make them far superior over other types of grafts. The most common donor site for bone grafting is the patient's own iliac crest. Because the autografts used here were the native osteotomized tibiae, they were far superior to autografts available in a clinical setting. This group represents a hypothetically perfect case scenario, in which an exact autologous replica of the lost bone was implanted within the fracture site. The autografts used in this study were structurally identical to the fractured site in size, shape and bone content. This allowed efficient bone formation and complete bridging of the defect in eight weeks, as seen in the Inventors' results. In addition, their harvest did not result in donor site morbidities, shortening the surgical time and improving recovery. Moreover, these autografts were attached to a periosteal blood supply. These factors were shown to improve fracture healing. It has been reported that this approach resulted in superior fracture repair relative to other types of grafts. The similarities found between the Autograft group and the group treated with BMP-6 and ultrasound application (BMP-6+US) serves as a proof of concept that the Inventors' proposed therapy is as efficient as an "optimal" autograft for the treatment of critical-sized fractures, which is not always available in all clinical cases.

A final difference between the Inventors' study and that of other reports is the use of ultrasound imaging to monitor microbubble oscillation during treatment. This is a key aspect of the protocol since while ultrasound therapy is highly promising, ultrasound wave propagation is limited by the medium it can be applied upon. Both bone and fixation plates are highly reflective of ultrasound waves. These reflections can significantly change the ultrasound field in the fracture site lowering transfection efficacy. This effect was observed in other works, requiring longer ultrasound exposure time for effective gene delivery. For efficient gene delivery using the Inventors' proposed therapy, imaging provides the opportunity to insure sufficient sonoporation in spite of the fixation plates that have the potential to impede the ultrasonic waves. More robust ultrasound systems can be implemented to bypass these hurdles in future human therapies. One of the parameters not tested in this study is the use of repeated treatments. Due to the therapy's relative ease and low invasiveness, repeated treatments at various time points might further enhance the effect of osteogenesis and promote faster and improved bone repair. Thus, implementation of multiple treatments could be another approach in future ultrasound-mediated gene delivery studies. However, it must be noted that excess DNA delivery to the cells could result in cellular toxicity via a mechanical mechanism. Additionally, prolonged ultrasound exposure could result in a variety of adverse effects, including excessive tissue heating and dystrophic calcifications due to tissue damage. With higher ultrasound intensities, the combination of ultrasound and microbubbles can also result in cellular lysis due to jetting during microbubble collapse within the tissue.

The current study evaluated the effect of ultrasound-based BMP gene delivery for a short term. A long-term study is required to fully assess the efficiency of the method in bone healing compared to controls. Here the Inventors implanted in all animals a collagen scaffold that the Inventors have previously shown to have some osteoconductive properties. Yet, even with the inclusion of the scaffold, and within a short period of time, the Inventors were able to show significant results in union rate, bone formation and biomechanics between the groups. The Inventors can determine that the combined therapy of a collagen scaffold, BMP-6 plasmid, microbubbles and ultrasound is superior to the control groups and is similar to autograft treated animals. There is much debate whether low-intensity pulsed ultrasound (LIPUS) can accelerate fracture healing. A recent study showed that ultrasound alone does not improve functional recovery or accelerate radiographic healing of tibial fractures in human patients. In addition, LIPUS is applied daily for weeks (up to 52 weeks in the above-mentioned study), while the Inventors' proposed therapy only required a single exposure, making it less likely that ultrasound alone has an effect on fracture repair. Also, the Inventors' data analysis showed no differences in bone formation between the group treated with ultrasound and an empty plasmid suspended in microbubbles ("US only" group) compared to the negative control group ("Scaffold only" group), further supporting the Inventors' hypothesis that the therapeutic effect was achieved via localized gene delivery.

These results show great promise for future ultrasound-mediated gene therapies to tissues. Since ultrasound technology is safe and widely used in the clinic, this approach can easily be translated into clinical practice. The introduction of microbubbles allows localization of the injected material and real-time monitoring of the sonoporation procedure in the treated site. This method has the potential to be used for many different applications, promoting in situ tissue engineering. In the context of bone fractures, this therapy can be applied to a variety of orthopedic indications. It is minimally invasive, does not require ex vivo stem cell manipulation, and avoids use of costly growth factors or the patient's own bone harvest for implantation. Since no alternative efficient method of inducing bone regeneration in sites with severe bone loss has yet been found, ultrasound-mediated gene therapy is a promising tool that might offer a positive response to this unmet clinical need.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, agents used for recruiting endogenous stem cells, plasmids and the proteins encoded by said plasmids, methods of delivering plasmids, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of promoting osseointegration in a soft-tissue structure injury of the musculoskeletal system of a patient, comprising the steps of:
   administering an agent comprising a collagen scaffold at an injured soft-tissue site of the musculoskeletal system of a patient, the injured soft-tissue site comprising an interface of: (i) bone and (ii) tendon or ligament,
   wherein the injured soft-tissue site comprises injured soft-tissue,
   wherein the soft tissue site includes one or more bone tunnel;
   recruiting endogenous mesenchymal stem cells to the injured soft-tissue site by the agent comprising a collagen scaffold;
   delivering a non-viral composition comprising 0.6-1.0 mg of bone morphogenic protein-6 (BMP-6) encoding plasmid suspended in $10^5$-$10^8$ microbubbles per 1-3 $cm^3$ of one or more bone tunnel at the injured soft-tissue site,
      wherein the non-viral composition is delivered 14 days after administration of the agent comprising the collagen scaffold;
   applying ultrasound to the injured soft-tissue site after delivery of the non-viral composition; and visualizing microbubble oscillation using ultrasound imaging, wherein the recruited endogenous mesenchymal stem cells at the injured soft-tissue site are transfected with the delivered non-viral composition and express BMP-6; and wherein the injured soft-tissue is selected from the group consisting of anterior cruciate ligament, posterior cruciate ligament, medial collateral ligament of the knee, medial collateral ligament of the elbow, lateral collateral ligament of the knee, lateral collateral ligament of the elbow, and rotator cuff tendon.

2. The method of claim 1, wherein the non-viral composition comprising 0.6-1.0 mg of BMP-6 encoding plasmid suspended in $10^5$-$10^8$ microbubbles per 1-3 cm$^3$ of one or more bone tunnel at the injured soft-tissue site is delivered in only one dose.

3. The method of claim 1, wherein applying ultrasound to the injured soft-tissue site is completed with a transmission frequency of 1.0-1.5 MHz.

4. The method of claim 1, wherein applying ultrasound to the injured soft-tissue site is completed with a mechanical index of 0.3-0.9.

5. The method of claim 1, wherein applying ultrasound to the injured soft-tissue site is completed for 30 seconds to 5 minutes.

6. The method of claim 1, wherein applying ultrasound to the injured soft-tissue site is completed with a transmission frequency of 1.3 MHz, a mechanical index of 0.6, and a depth of 4 cm for approximately 2 minutes until all visualized microbubbles of the non-viral composition burst.

7. The method of claim 1, wherein applying ultrasound to the injured soft-tissue site is completed until all visualized microbubbles of the non-viral composition burst.

8. The method of claim 1, further comprising the step of measuring osseointegration via computer tomography scan or magnetic resonance imaging after applying ultrasound to the injured soft-tissue site.

9. The method of claim 1, further comprising locating the injured soft-tissue site using fluoroscopic imaging prior to delivering the non-viral composition.

10. The method of claim 1, wherein the non-viral composition includes 1.0 mg of BMP-6 encoding plasmid suspended in $10^7$ microbubbles per 1-3 cm$^3$ of one or more bone tunnel.

11. The method of claim 1, wherein the recruited endogenous mesenchymal stem cells populate the collagen scaffold at the injured soft-tissue site.

12. The method of claim 1, wherein the non-viral composition is delivered to the injured soft-tissue site through a needle of a syringe.

13. The method of claim 12, further comprising placing an ultrasound probe adjacent to the needle for visualization of the delivered non-viral composition and for applying ultrasound to the injured soft-tissue site.

14. The method of claim 13, wherein microbubble oscillation is monitored using ultrasound imaging while applying ultrasound to the injured soft-tissue site at which the non-viral composition has been delivered.

* * * * *